United States Patent
Abbate et al.

(10) Patent No.: US 9,782,283 B2
(45) Date of Patent: *Oct. 10, 2017

(54) METHODS AND DEVICES FOR CRIMPING SELF-EXPANDING DEVICES

(71) Applicant: Intersect ENT, Inc., Menlo Park, CA (US)

(72) Inventors: Anthony J. Abbate, Santa Clara, CA (US); Bin Huang, Pleasanton, CA (US); Gail M. Zaler, Milpitas, CA (US); David C. Gale, Kennesaw, GA (US); Richard E. Kaufman, Los Gatos, CA (US); Vijaykumar Rajasekhar, Apple Valley, CA (US)

(73) Assignee: Intersect ENT, Inc., Menlo Park, CA (US)

( * ) Notice: Subject to any disclaimer, the term of this patent is extended or adjusted under 35 U.S.C. 154(b) by 355 days.

This patent is subject to a terminal disclaimer.

(21) Appl. No.: 14/298,715

(22) Filed: Jun. 6, 2014

(65) Prior Publication Data

US 2014/0283349 A1 Sep. 25, 2014

Related U.S. Application Data

(63) Continuation of application No. 12/512,855, filed on Jul. 30, 2009, now Pat. No. 8,763,222.

(Continued)

(51) Int. Cl.
*B23P 19/00* (2006.01)
*A61F 2/95* (2013.01)
(Continued)

(52) U.S. Cl.
CPC ................ *A61F 2/95* (2013.01); *B25B 27/10* (2013.01); *A61F 2/0095* (2013.01); *A61F 2/24* (2013.01);
(Continued)

(58) Field of Classification Search
CPC ... B23Q 1/03; B23Q 1/00; B23Q 1/28; B23Q 3/06; B23Q 3/00; B23P 19/04
See application file for complete search history.

(56) References Cited

U.S. PATENT DOCUMENTS

| 374,026 A | 11/1887 | Williams |
| 2,096,162 A | 10/1937 | Daley |

(Continued)

FOREIGN PATENT DOCUMENTS

| AU | 2008/201495 A1 | 10/2008 |
| DE | 101 05 592 A1 | 8/2002 |

(Continued)

OTHER PUBLICATIONS

Becker, D.G. (2003). "The Minimally Invasive, Endoscopic Approach to Sinus Surgery," *Journal of Long-Term Effects of Medical Implants* 13(3):207-221.

(Continued)

*Primary Examiner* — Lee D Wilson
(74) *Attorney, Agent, or Firm* — Cooley LLP

(57) ABSTRACT

Described here are devices and methods for crimping self-expanding devices. The crimping devices may be useful for crimping a variety of different self-expanding devices (whether such devices are biodegradable or bio-durable). The crimping devices may have crimping members to engage the self-expanding device to reduce the device from an expanding configuration to an unexpanded configuration. The crimping member may comprise or include a suture, wire, ribbon, guiding hoop, pusher, prong, holding bar, balloon, jaws, combinations thereof, or the like. The crimping devices may also include or comprise a holding structure to hold the self-expanding device in an unexpanded or expanded configuration.

8 Claims, 22 Drawing Sheets

Related U.S. Application Data

(60) Provisional application No. 61/085,795, filed on Aug. 1, 2008.

(51) Int. Cl.
*B25B 27/10* (2006.01)
*A61F 2/00* (2006.01)
*A61F 2/24* (2006.01)

(52) U.S. Cl.
CPC .............. *A61F 2002/9511* (2013.01); *A61F 2002/9522* (2013.01); *Y10T 29/49908* (2015.01); *Y10T 29/53657* (2015.01); *Y10T 29/53709* (2015.01); *Y10T 29/53783* (2015.01); *Y10T 29/53991* (2015.01)

(56) References Cited

U.S. PATENT DOCUMENTS

| | | |
|---|---|---|
| 2,691,985 A | 10/1954 | Newsom |
| 3,049,125 A | 8/1962 | Kriwkowitsch |
| 3,473,165 A | 10/1969 | Gran et al. |
| 3,502,078 A | 3/1970 | Hill et al. |
| 3,570,494 A | 3/1971 | Gottschalk |
| 3,583,391 A | 6/1971 | Cox et al. |
| 3,766,924 A | 10/1973 | Pidgeon |
| 3,800,788 A | 4/1974 | White |
| 3,894,539 A | 7/1975 | Tallent |
| 3,903,893 A | 9/1975 | Scheer |
| 3,913,584 A | 10/1975 | Walchle et al. |
| 4,094,303 A | 6/1978 | Johnston |
| 4,245,652 A | 1/1981 | Kelly et al. |
| 4,389,208 A | 6/1983 | LeVeen et al. |
| 4,419,095 A | 12/1983 | Nebergall et al. |
| D276,937 S | 12/1984 | Griggs |
| 4,534,761 A | 8/1985 | Raible |
| 4,580,568 A | 4/1986 | Gianturco |
| 4,604,920 A | 8/1986 | Dupke |
| 4,627,971 A | 12/1986 | Ayer |
| 4,650,488 A | 3/1987 | Bays et al. |
| 4,655,771 A | 4/1987 | Wallsten |
| 4,704,126 A | 11/1987 | Baswell et al. |
| 4,737,141 A | 4/1988 | Spits |
| 4,744,792 A | 5/1988 | Sander et al. |
| 4,753,636 A | 6/1988 | Free |
| 4,886,493 A | 12/1989 | Yee |
| 4,941,881 A | 7/1990 | Masters et al. |
| 4,964,850 A | 10/1990 | Bouton et al. |
| 5,000,957 A | 3/1991 | Eckenhoff et al. |
| 5,011,474 A | 4/1991 | Brennan |
| 5,035,706 A | 7/1991 | Giantureo et al. |
| 5,062,829 A | 11/1991 | Pryor et al. |
| 5,116,311 A | 5/1992 | Löfstedt |
| 5,139,502 A | 8/1992 | Berg et al. |
| 5,139,510 A | 8/1992 | Goldsmith, III et al. |
| 5,139,832 A | 8/1992 | Hayashi et al. |
| 5,167,614 A | 12/1992 | Tessmann et al. |
| 5,189,110 A | 2/1993 | Ikematu et al. |
| 5,246,455 A | 9/1993 | Shikani |
| 5,256,146 A | 10/1993 | Ensminger et al. |
| 5,300,119 A | 4/1994 | Blom |
| 5,312,813 A | 5/1994 | Costerton et al. |
| 5,336,163 A | 8/1994 | DeMane et al. |
| 5,342,296 A | 8/1994 | Persson et al. |
| 5,348,553 A | 9/1994 | Whitney |
| 5,350,580 A | 9/1994 | Muchow et al. |
| 5,391,179 A | 2/1995 | Mezzoli |
| 5,443,498 A | 8/1995 | Fontaine |
| 5,501,700 A | 3/1996 | Hirata |
| 5,507,210 A | 4/1996 | Paramest |
| 5,507,807 A | 4/1996 | Shippert |
| 5,512,055 A | 4/1996 | Domb et al. |
| 5,538,738 A | 7/1996 | Ritter et al. |
| 5,540,712 A | 7/1996 | Kleshinski et al. |
| 5,556,413 A | 9/1996 | Lam |
| 5,632,762 A | 5/1997 | Myler |
| 5,645,584 A | 7/1997 | Suyama |
| 5,664,567 A | 9/1997 | Linder |
| 5,672,179 A | 9/1997 | Garth et al. |
| 5,693,065 A | 12/1997 | Rains, III |
| 5,713,855 A | 2/1998 | Shippert |
| 5,746,224 A | 5/1998 | Edwards |
| 5,749,921 A | 5/1998 | Lenker et al. |
| 5,792,100 A | 8/1998 | Shantha |
| 5,800,379 A | 9/1998 | Edwards |
| 5,800,429 A | 9/1998 | Edwards |
| 5,827,224 A | 10/1998 | Shippert |
| 5,899,878 A | 5/1999 | Glassman |
| 5,928,190 A | 7/1999 | Davis |
| 5,992,000 A | 11/1999 | Humphrey et al. |
| 6,033,436 A | 3/2000 | Steinke et al. |
| 6,054,122 A | 4/2000 | MacPhee et al. |
| 6,063,102 A | 5/2000 | Morales |
| 6,074,381 A | 6/2000 | Dinh et al. |
| 6,082,990 A | 7/2000 | Jackson et al. |
| 6,092,273 A | 7/2000 | Villareal |
| 6,092,528 A | 7/2000 | Edwards |
| 6,108,886 A | 8/2000 | Kimes et al. |
| 6,113,641 A | 9/2000 | Leroy et al. |
| 6,123,697 A | 9/2000 | Shippert |
| 6,149,681 A | 11/2000 | Houser et al. |
| 6,149,944 A | 11/2000 | Jeong et al. |
| 6,152,946 A | 11/2000 | Broome et al. |
| 6,180,848 B1 | 1/2001 | Flament et al. |
| 6,190,353 B1 | 2/2001 | Makower et al. |
| 6,195,225 B1 | 2/2001 | Komatsu et al. |
| 6,200,335 B1 | 3/2001 | Igaki |
| 6,224,626 B1 | 5/2001 | Steinke |
| 6,228,111 B1 | 5/2001 | Törmälä et al. |
| 6,280,413 B1 | 8/2001 | Clark et al. |
| 6,290,728 B1 | 9/2001 | Phelps et al. |
| 6,297,227 B1 | 10/2001 | Johnson |
| 6,302,875 B1 | 10/2001 | Makower et al. |
| 6,306,084 B1 | 10/2001 | Pinczower |
| 6,342,068 B1 | 1/2002 | Thompson |
| 6,347,241 B2 | 2/2002 | Burbank et al. |
| 6,350,465 B1 | 2/2002 | Jonnalagadda et al. |
| 6,352,547 B1 | 3/2002 | Brown et al. |
| 6,355,032 B1 | 3/2002 | Hovda et al. |
| 6,375,615 B1 | 4/2002 | Flaherty et al. |
| 6,386,197 B1 | 5/2002 | Miller |
| 6,398,758 B1 | 6/2002 | Jacobsen et al. |
| 6,447,539 B1 | 9/2002 | Nelson et al. |
| 6,491,940 B1 | 12/2002 | Levin |
| 6,524,608 B2 | 2/2003 | Ottoboni et al. |
| 6,537,294 B1 | 3/2003 | Boyle et al. |
| 6,543,452 B1 | 4/2003 | Lavigne |
| 6,544,230 B1 | 4/2003 | Flaherty et al. |
| 6,555,566 B2 | 4/2003 | Ponikau |
| 6,562,058 B2 | 5/2003 | Seguin et al. |
| 6,565,597 B1 | 5/2003 | Fearnot et al. |
| 6,589,286 B1 | 7/2003 | Litner |
| 6,605,294 B2 | 8/2003 | Sawhney |
| 6,606,995 B1 | 8/2003 | Sadek et al. |
| 6,618,921 B1 | 9/2003 | Thornton |
| 6,685,648 B2 | 2/2004 | Flaherty et al. |
| 6,692,455 B2 | 2/2004 | Goode et al. |
| 6,695,856 B2 | 2/2004 | Kieturakis et al. |
| 6,709,465 B2 | 3/2004 | Mitchell et al. |
| 6,712,859 B2 | 3/2004 | Rousseau et al. |
| 6,715,485 B1 | 4/2004 | Djupesland |
| 6,719,934 B2 | 4/2004 | Stinson |
| 6,746,426 B1 | 6/2004 | Flaherty et al. |
| 6,749,617 B1 | 6/2004 | Palasis et al. |
| 6,884,260 B2 | 4/2005 | Kugler et al. |
| 6,942,690 B1 | 9/2005 | Pollock et al. |
| 6,945,992 B2 | 9/2005 | Goodson, IV et al. |
| 6,951,053 B2 | 10/2005 | Padilla et al. |
| 6,966,923 B2 | 11/2005 | Gittings |
| 7,018,401 B1 | 3/2006 | Hyodoh et al. |
| 7,072,720 B2 | 7/2006 | Puskas |
| 7,074,426 B2 | 7/2006 | Kochinke |
| 7,108,706 B2 | 9/2006 | Hogle |
| RE39,321 E | 10/2006 | MacPhee et al. |

(56) References Cited

U.S. PATENT DOCUMENTS

| | | |
|---|---|---|
| 7,195,016 B2 | 3/2007 | Loyd et al. |
| 7,225,518 B2 | 6/2007 | Eidenschink et al. |
| 7,235,099 B1 | 6/2007 | Duncavage et al. |
| 7,249,390 B2 | 7/2007 | Yale et al. |
| RE39,923 E | 11/2007 | Blom |
| 7,314,484 B2 | 1/2008 | Deem et al. |
| 7,316,147 B2 | 1/2008 | Perreault et al. |
| 7,361,168 B2 | 4/2008 | Makower et al. |
| 7,410,480 B2 | 8/2008 | Muni et al. |
| 7,419,497 B2 | 9/2008 | Muni et al. |
| 7,451,765 B2 | 11/2008 | Adler |
| 7,462,175 B2 | 12/2008 | Chang et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,559,925 B2 | 7/2009 | Goldfarb et al. |
| 7,641,644 B2 | 1/2010 | Chang et al. |
| 7,641,688 B2 | 1/2010 | Lesh |
| 7,645,272 B2 | 1/2010 | Chang et al. |
| 7,651,696 B2 | 1/2010 | Bates |
| 7,654,997 B2 | 2/2010 | Makower et al. |
| 7,658,758 B2 | 2/2010 | Diaz et al. |
| 7,658,764 B2 | 2/2010 | Reitan et al. |
| 7,662,141 B2 | 2/2010 | Eaton et al. |
| 7,662,142 B2 | 2/2010 | Eaton et al. |
| 7,686,798 B2 | 3/2010 | Eaton et al. |
| 7,691,094 B2 | 4/2010 | Eaton et al. |
| 7,713,255 B2 | 5/2010 | Eaton et al. |
| 7,717,933 B2 | 5/2010 | Becker |
| 7,740,642 B2 | 6/2010 | Becker |
| 7,753,929 B2 | 7/2010 | Becker |
| 7,771,482 B1 | 8/2010 | Karmon |
| 7,951,130 B2 | 5/2011 | Eaton et al. |
| 7,951,131 B2 | 5/2011 | Eaton et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 8,025,635 B2 | 9/2011 | Eaton et al. |
| 8,088,120 B2 | 1/2012 | Worsoff |
| 8,109,918 B2 | 2/2012 | Eaton et al. |
| 8,192,450 B2 | 6/2012 | Gonzales et al. |
| 8,197,433 B2 | 6/2012 | Cohen |
| 8,303,640 B2 | 11/2012 | Hepworth et al. |
| 8,337,454 B2 | 12/2012 | Eaton et al. |
| 8,500,776 B2 | 8/2013 | Ebner |
| 8,535,707 B2 | 9/2013 | Arensdorf et al. |
| 8,585,730 B2 | 11/2013 | Eaton et al. |
| 8,585,731 B2 | 11/2013 | Abbate et al. |
| 8,585,753 B2 | 11/2013 | Scanlon et al. |
| 8,721,591 B2 | 5/2014 | Chang et al. |
| 8,740,029 B2 | 6/2014 | Barnoski et al. |
| 8,740,839 B2 | 6/2014 | Eaton et al. |
| 8,740,929 B2 | 6/2014 | Gopferich et al. |
| 8,763,222 B2 * | 7/2014 | Abbate ............... A61F 2/95  29/243.5 |
| 8,802,131 B2 | 8/2014 | Arensdorf et al. |
| 8,858,974 B2 | 10/2014 | Eaton et al. |
| 8,986,341 B2 | 3/2015 | Abbate et al. |
| 2002/0022048 A1 | 2/2002 | Bromberg et al. |
| 2002/0051793 A1 | 5/2002 | Drabick |
| 2002/0051845 A1 | 5/2002 | Mehta et al. |
| 2002/0077693 A1 | 6/2002 | Barclay et al. |
| 2002/0111603 A1 | 8/2002 | Cheikh |
| 2002/0143387 A1 | 10/2002 | Soetikno et al. |
| 2002/0188344 A1 | 12/2002 | Bolea et al. |
| 2002/0198586 A1 | 12/2002 | Inoue |
| 2003/0055488 A1 | 3/2003 | Igaki |
| 2003/0065346 A1 | 4/2003 | Evens et al. |
| 2003/0070682 A1 | 4/2003 | Wilson et al. |
| 2003/0105469 A1 | 6/2003 | Karmon |
| 2003/0133877 A1 | 7/2003 | Levin |
| 2003/0135266 A1 | 7/2003 | Chew et al. |
| 2003/0135268 A1 | 7/2003 | Desai |
| 2003/0135970 A1 | 7/2003 | Thornton |
| 2003/0147954 A1 | 8/2003 | Yang et al. |
| 2003/0158598 A1 | 8/2003 | Ashton |
| 2003/0195459 A1 | 10/2003 | Shippert |
| 2003/0203030 A1 | 10/2003 | Ashton et al. |
| 2003/0209835 A1 | 11/2003 | Chun et al. |
| 2003/0236570 A1 | 12/2003 | Cook et al. |
| 2004/0043052 A1 | 3/2004 | Hunter et al. |
| 2004/0064083 A1 | 4/2004 | Becker |
| 2004/0064150 A1 | 4/2004 | Becker |
| 2004/0093062 A1 | 5/2004 | Glastra |
| 2004/0116958 A1 | 6/2004 | Gopferich et al. |
| 2004/0117004 A1 | 6/2004 | Osborne et al. |
| 2004/0133270 A1 | 7/2004 | Grandt |
| 2004/0176827 A1 | 9/2004 | Jacobson et al. |
| 2004/0236415 A1 | 11/2004 | Thomas |
| 2005/0038497 A1 | 2/2005 | Neuendorf et al. |
| 2005/0043783 A1 | 2/2005 | Amis et al. |
| 2005/0119725 A1 | 6/2005 | Wang et al. |
| 2005/0124560 A1 | 6/2005 | Sung et al. |
| 2005/0131460 A1 | 6/2005 | Gilford |
| 2005/0131514 A1 | 6/2005 | Hijlkema et al. |
| 2005/0131525 A1 | 6/2005 | Hartley |
| 2005/0143817 A1 | 6/2005 | Hunter et al. |
| 2005/0165347 A1 | 7/2005 | Bardy |
| 2005/0203605 A1 | 9/2005 | Dolan |
| 2005/0229670 A1 | 10/2005 | Perreault |
| 2005/0240147 A1 | 10/2005 | Makower et al. |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0095066 A1 | 5/2006 | Chang et al. |
| 2006/0106361 A1 | 5/2006 | Muni et al. |
| 2006/0135981 A1 | 6/2006 | Lenker et al. |
| 2006/0142736 A1 | 6/2006 | Hissink et al. |
| 2006/0162722 A1 | 7/2006 | Boehm et al. |
| 2006/0167540 A1 | 7/2006 | Masters et al. |
| 2006/0210605 A1 | 9/2006 | Chang et al. |
| 2006/0247499 A1 | 11/2006 | Butler et al. |
| 2006/0265042 A1 | 11/2006 | Catanese, III et al. |
| 2006/0276871 A1 | 12/2006 | Lamson et al. |
| 2007/0055348 A1 | 3/2007 | Pryor |
| 2007/0079494 A1 | 4/2007 | Serrano |
| 2007/0100435 A1 | 5/2007 | Case et al. |
| 2007/0106366 A1 | 5/2007 | Delaloye et al. |
| 2007/0129751 A1 | 6/2007 | Muni et al. |
| 2007/0135789 A1 | 6/2007 | Chang et al. |
| 2007/0156211 A1 | 7/2007 | Ferren et al. |
| 2007/0162100 A1 | 7/2007 | Gabbay |
| 2007/0167682 A1 | 7/2007 | Goldfarb et al. |
| 2007/0179599 A1 | 8/2007 | Brodbeck et al. |
| 2007/0191922 A1 | 8/2007 | Hartley |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0227544 A1 | 10/2007 | Betsy et al. |
| 2007/0233225 A1 | 10/2007 | Rapacki et al. |
| 2007/0249896 A1 | 10/2007 | Goldfarb et al. |
| 2007/0250105 A1 | 10/2007 | Ressemann et al. |
| 2007/0269385 A1 | 11/2007 | Yun et al. |
| 2007/0270941 A1 | 11/2007 | Headley et al. |
| 2007/0282305 A1 | 12/2007 | Goldfarb et al. |
| 2007/0293726 A1 | 12/2007 | Goldfarb et al. |
| 2007/0293727 A1 | 12/2007 | Goldfarb et al. |
| 2007/0293946 A1 | 12/2007 | Gonzales et al. |
| 2007/0297186 A1 | 12/2007 | Hoover et al. |
| 2007/0299043 A1 | 12/2007 | Hunter et al. |
| 2008/0015540 A1 | 1/2008 | Muni et al. |
| 2008/0058295 A1 | 3/2008 | Chaudry |
| 2008/0058296 A1 | 3/2008 | Chaudry |
| 2008/0069858 A1 | 3/2008 | Weber |
| 2008/0077226 A1 | 3/2008 | Ouellette et al. |
| 2008/0077230 A1 | 3/2008 | Heaney et al. |
| 2008/0082162 A1 | 4/2008 | Boismier et al. |
| 2008/0085293 A1 | 4/2008 | Yang |
| 2008/0089952 A1 | 4/2008 | Hunter et al. |
| 2008/0097154 A1 | 4/2008 | Makower et al. |
| 2008/0097239 A1 | 4/2008 | Chang et al. |
| 2008/0097295 A1 | 4/2008 | Makower et al. |

(56) References Cited

U.S. PATENT DOCUMENTS

| | | |
|---|---|---|
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0097568 A1 | 4/2008 | Savage et al. |
| 2008/0097575 A1 | 4/2008 | Cottone |
| 2008/0097576 A1 | 4/2008 | Cottone et al. |
| 2008/0097580 A1 | 4/2008 | Dave |
| 2008/0097581 A1 | 4/2008 | Shanley |
| 2008/0097591 A1 | 4/2008 | Savage et al. |
| 2008/0103361 A1 | 5/2008 | Makower et al. |
| 2008/0103521 A1 | 5/2008 | Makower et al. |
| 2008/0103584 A1 | 5/2008 | Su et al. |
| 2008/0113000 A1 | 5/2008 | Hunter et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0145514 A1 | 6/2008 | Hunter et al. |
| 2008/0154237 A1 | 6/2008 | Chang et al. |
| 2008/0154250 A1 | 6/2008 | Makower et al. |
| 2008/0183128 A1 | 7/2008 | Morriss et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0262593 A1 | 10/2008 | Ryan et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306579 A1 | 12/2008 | Dolan et al. |
| 2008/0319424 A1 | 12/2008 | Muni et al. |
| 2009/0004272 A1 | 1/2009 | Gibson et al. |
| 2009/0004273 A1 | 1/2009 | Gibson et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0035351 A1 | 2/2009 | Berglund et al. |
| 2009/0036968 A1 | 2/2009 | Hepworth et al. |
| 2009/0036974 A1 | 2/2009 | Penn et al. |
| 2009/0041824 A1 | 2/2009 | Zugates et al. |
| 2009/0056709 A1 | 3/2009 | Worsoff |
| 2009/0093823 A1 | 4/2009 | Chang et al. |
| 2009/0187098 A1 | 7/2009 | Makower et al. |
| 2009/0198179 A1 | 8/2009 | Abbate et al. |
| 2009/0198216 A1 | 8/2009 | Muni et al. |
| 2009/0240112 A1 | 9/2009 | Goldfarb et al. |
| 2009/0312745 A1 | 12/2009 | Goldfarb et al. |
| 2010/0043197 A1* | 2/2010 | Abbate ............... A61F 2/95 29/505 |
| 2011/0004192 A1 | 1/2011 | Eaton et al. |
| 2011/0021986 A1 | 1/2011 | Zamboni |
| 2011/0167964 A1 | 7/2011 | Price |
| 2012/0101429 A1 | 4/2012 | Eaton et al. |
| 2013/0041463 A1 | 2/2013 | Ressemann |
| 2013/0066358 A1 | 3/2013 | Nalluri et al. |
| 2013/0231693 A1 | 9/2013 | Edgren et al. |
| 2013/0245608 A1 | 9/2013 | Muni et al. |
| 2013/0253567 A1 | 9/2013 | Edgren et al. |
| 2013/0281982 A1 | 10/2013 | Makower et al. |
| 2013/0304232 A1 | 11/2013 | Gries |
| 2014/0018839 A1 | 1/2014 | Renner et al. |
| 2014/0074065 A1 | 3/2014 | Muni et al. |
| 2014/0079755 A1 | 3/2014 | Eaton et al. |
| 2014/0107615 A1 | 4/2014 | Doshi et al. |
| 2014/0283349 A1* | 9/2014 | Abbate ............... A61F 2/95 29/235 |
| 2014/0324025 A1 | 10/2014 | Arensdorf et al. |
| 2015/0081017 A1 | 3/2015 | Abbate et al. |
| 2016/0287854 A1 | 10/2016 | Eaton et al. |

FOREIGN PATENT DOCUMENTS

| | | |
|---|---|---|
| EP | 0 423 916 A1 | 4/1991 |
| EP | 0 761 251 A1 | 3/1997 |
| EP | 0 938 880 A2 | 9/1999 |
| EP | 1 415 671 A1 | 5/2004 |
| EP | 1 870 057 A1 | 12/2007 |
| JP | 2-500521 A | 2/1990 |
| JP | 04-25755 U | 2/1992 |
| JP | 6-5800 Y2 | 2/1994 |
| JP | 6-506672 A | 7/1994 |
| JP | 6-329542 A | 11/1994 |
| JP | 8-117326 A | 5/1996 |
| JP | 2000-507630 A | 6/2000 |
| JP | 2001-506144 A | 5/2001 |
| JP | 2001-520188 A | 10/2001 |
| WO | WO-89/00839 A1 | 2/1989 |
| WO | WO-97/36949 A1 | 10/1997 |
| WO | WO-99/20261 A2 | 4/1999 |
| WO | WO-99/20261 A3 | 4/1999 |
| WO | WO-01/02024 A1 | 1/2001 |
| WO | WO-01/02024 C1 | 1/2001 |
| WO | WO-01/26658 A2 | 4/2001 |
| WO | WO-01/26658 A3 | 4/2001 |
| WO | WO-01/30411 A1 | 5/2001 |
| WO | WO-01/95834 A1 | 12/2001 |
| WO | WO-03/090818 A2 | 11/2003 |
| WO | WO-03/090818 A3 | 11/2003 |
| WO | WO-03/099359 A1 | 12/2003 |
| WO | WO-2004/016200 A1 | 2/2004 |
| WO | WO-2004/082525 A2 | 9/2004 |
| WO | WO-2004/082525 A3 | 9/2004 |
| WO | WO-2006/020180 A2 | 2/2006 |
| WO | WO-2006/020180 A3 | 2/2006 |
| WO | WO-2006/107957 A2 | 10/2006 |
| WO | WO-2006/107957 A3 | 10/2006 |
| WO | WO-2007/067451 A2 | 6/2007 |
| WO | WO-2007/067451 A3 | 6/2007 |
| WO | WO-2007/134215 A2 | 11/2007 |
| WO | WO-2007/134215 A3 | 11/2007 |
| WO | WO-2007/139668 A2 | 12/2007 |
| WO | WO-2007/139668 A3 | 12/2007 |
| WO | WO-2008/008389 A2 | 1/2008 |
| WO | WO-2008/008389 A3 | 1/2008 |
| WO | WO-2008/033533 A2 | 3/2008 |
| WO | WO-2008/033533 A3 | 3/2008 |
| WO | WO-2008/051453 A2 | 5/2008 |
| WO | WO-2008/051453 A3 | 5/2008 |
| WO | WO-2008/051881 A2 | 5/2008 |
| WO | WO-2008/051881 A3 | 5/2008 |
| WO | WO-2008/054655 A2 | 5/2008 |
| WO | WO-2008/054655 A3 | 5/2008 |
| WO | WO-2008/070996 A1 | 6/2008 |
| WO | WO-2008/154143 A2 | 12/2008 |
| WO | WO-2008/154143 A3 | 12/2008 |
| WO | WO-2009/079418 A2 | 6/2009 |
| WO | WO-2009/079418 A3 | 6/2009 |
| WO | WO-2010/014834 A1 | 2/2010 |
| WO | WO-2012/083594 A1 | 6/2012 |
| WO | WO-2012/107229 A1 | 8/2012 |
| WO | WO-2013/158337 A1 | 10/2013 |

OTHER PUBLICATIONS

Eberhart, R.C. et al. (2003). "Bioresorbable Polymeric Stents: Current Status and Future Promise," *J. Biomater. Sci. Polymer Edn.* 14(4):299-312.

European Search Report mailed on Feb. 21, 2011, for EP Patent Application No. 10011116.0 filed on Apr. 4, 2006, 9 pages.

European Search Report mailed on Feb. 21, 2011, for EP Patent Application No. 10011117.8 filed on Apr. 4, 2006, 9 pages.

European Search Report mailed on Feb. 21, 2011, for EP Patent Application No. 10011118.6 filed on Apr. 4, 2006, 9 pages.

European Office Action mailed on Mar. 6, 2015, for EP Patent Application No. 10 011 116.0, filed on Apr. 4, 2006, 4 pages.

European Office Action mailed on Mar. 6, 2015, for EP Patent Application No. 10 011 117.8, filed on Apr. 4, 2006, 4 pages.

(56) References Cited

OTHER PUBLICATIONS

European Office Action mailed on Mar. 10, 2015, for EP Patent Application No. 10 011 118.6, filed on Apr. 4, 2006, 5 pages.
Final Office Action mailed on Jan. 8, 2009, for U.S. Appl. No. 10/800,162, filed Mar. 12, 2004, 5 pages.
Final Office Action mailed on Jul. 22, 2009, for U.S. Appl. No. 11/398,342, filed Apr. 4, 2006, 8 pages.
Final Office Action mailed on Jul. 8, 2010, for U.S. Appl. No. No. 11/398,342, filed Apr. 4, 2006, 7 pages.
Final Office Action mailed on Aug. 18, 2010, for U.S. Appl. No. 11/775,157, filed Jul. 9, 2007, 12 pages.
Final Office Action mailed on Jan. 27, 2011, for U.S. Appl. No. 12/479,794, filed Jun. 6, 2009, 6 pages.
Final Office Action mailed on Nov. 28, 2011, for U.S. Appl. No. 12/883,071, filed Sep. 15, 2010, 7 pages.
Final Office Action mailed on Mar. 1, 2012, for U.S. Appl. No. 12/270,695, filed Nov. 13, 2008, 26 pages.
Final Office Action mailed on Apr. 12, 2012, for U.S. Appl. No. 12/883,087, filed Sep. 15, 2010, 7 pages.
Final Office Action mailed on Apr. 16, 2012, for U.S. Appl. No. 12/334,373, filed Dec. 12, 2008, 7 pages.
Final Office Action mailed on May 29, 2012, for U.S. Appl. No. 12/334,382, filed Dec. 12, 2008, 7 pages.
Final Office Action mailed on Mar. 6, 2013, for U.S. Appl. No. 13/341,732, filed Dec. 30, 2011, 7 pages.
Final Office Action mailed on May 30, 2013, for U.S. Appl. No. 12/541,840, filed Aug. 14, 2009, 11 pages.
Final Office Action mailed on Sep. 10, 2013, for U.S. Appl. No. 12/334,395, filed Dec. 12, 2008, 8 pages.
Final Office Action mailed on May 5, 2014 for U.S. Appl. No. 12/883,087, filed Sep. 15, 2010, 10 pages.
Final Office Action mailed on May 19, 2014, for U.S. Appl. No. 13/341,732, filed Dec. 30, 2011, 7 pages.
Final Office Action mailed on Sep. 17, 2014, for U.S. Appl. No. 12/334,395, filed Dec. 12, 2008, 10 pages.
Hietala, E-M. et al. (2001). "Biodegradation of the Copolymeric Polylactide Stent," *Journal of Vascular Research* 38:361-369.
Hosemann, W. et al. (Mar. 2003, e-pub. Oct. 10, 2002). "Innovative Frontal Sinus Stent Acting as a Local Drug-Releasing System," *Eur. Arch. Otorhinolaryngol.* 260:131-134.
International Search Report mailed on Sep. 28, 2009, for PCT Application No. PCT/US2009/052287, filed on Jul. 30, 2009, 2 pages.
Laaksovirta, S. (Aug. 22, 2003). *Biodegradable, Self-Reinforced, Self-Expandable Lactic and Glycolic Acid (SR-PLGA 80/20) Copolymer Spiral Prostatic Stent: Analysis of Mechanical and Biological Properties and Clinical Results*, Academic Dissertation, Medical School of the University of Tampere, 79 pages.
Lapchenko, A.S. et al. (Jun. 1996). "Polyphosphazene Prosthesis of the Frontonasal Bypass in Surgical Treatment of Acute and Chronic Inflammation of the Frontal Sinuses," *Vestnik Otorinolarinologii*, 2 pages.
Lavigne, F. et al. (May 2002). "Intrasinus Administration of Topical Budesonide to Allergic Patients With Chronic Rhinosinusitis Following Surgery," *The Laryngoscope* 112, 7 pages.
Min, Y-G. et al. (1995). "Application of Polylactic Acid Polymer in the Treatment of Acute Maxillary Sinusitis in Rabbits," *Acta Otolaryngol.* 115:548-552.
Min, Y-G. et al. (Aug. 1995). "Mucociliary Activity and Histopathology of Sinus Mucosa in Experimental Maxillary Sinusitis: A Comparison of Systemic Administration of Antibiotic and Antibiotic Delivery by Polylactic Acid Polymer," *The Laryngoscope* 105:835-842.
Murphy, J.G. et al. (1992). "Percutaneous Polymeric Stents in Porcine Coronary Arteries: Initial Experience With Polyethylene Terephthalate Stents," *Circulation* 86:1596-1604.
Nguyen, K.T. et al. (2004). "Biomaterials and Stent Technology," Chapter 5 in *Tissue Engineering and Novel Delivery Systems*, 24 pages.

Non-Final Office Action mailed on Jun. 6, 2008, for U.S. Appl. No. 10/800,162, filed Mar. 12, 2004, 5 pages.
Non-Final Office Action mailed on Nov. 25, 2008, for U.S. Appl. No. 11/398,342, filed Apr. 4, 2006, 10 pages.
Non-Final Office Action mailed on Sep. 22, 2009, for U.S. Appl. No. 12/419,927, filed Apr. 7, 2009, 4 pages.
Non-Final Office Action mailed on Sep. 22, 2009, for U.S. Appl. No. 12/419,943, filed Apr. 7, 2009, 5 pages.
Non-Final Office Action mailed on Sep. 22, 2009, for U.S. Appl. No. 12/419,930, filed Apr. 7, 2007, 4 pages.
Non-Final Office Action mailed on Sep. 22, 2009, for U.S. Appl. No. 12/419,937, filed Apr. 7, 2009, 4 pages.
Non-Final Office Action mailed on Sep. 22, 2009, for U.S. Appl. No. 12/419,925, filed Apr. 7, 2009, 4 pages.
Non-Final Office Action mailed on Nov. 13, 2009, for U.S. Appl. No. 11/398,342, filed Apr. 4, 2006, 9 pages.
Non-Final Office Action mailed on Dec. 9, 2009, for U.S. Appl. No. 11/775,157, filed Jul. 9, 2007, 12 pages.
Non-Final Office Action mailed on Jul. 1, 2010, for U.S. Appl. No. 12/479,794, filed Jun. 6, 2009, 5 pages.
Non-Final Office Action mailed on Sep. 10, 2010, for U.S. Appl. No. 12/437,374, filed May 7, 2009, 8 pages.
Non-Final Office Action mailed on Nov. 12, 2010, for U.S. Appl. No. 11/398,342, filed Apr. 4, 2006, 8 pages.
Non-Final Office Action mailed on Nov. 23, 2010, for U.S. Appl. No. 12/258,277, filed Oct. 24, 2008, 9 pages.
Non-Final Office Action mailed on Nov. 23, 2010, for U.S. Appl. No. 12/258,282, filed Oct. 24, 2008, 7 pages.
Non-Final Office Action mailed on Nov. 24, 2010, for U.S. Appl. No. 12/883,090, filed Sep. 15, 2010, 7 pages.
Non-Final Office Action mailed on Nov. 24, 2010, for U.S. Appl. No. 12/883,056, filed Sep. 15, 2010, 7 pages.
Non-Final Office Action mailed on Nov. 24, 2010, for U.S. Appl. No. 12/883,079, filed Sep. 15, 2010, 8 pages.
Non-Final Office Action mailed on Mar. 22, 2011, for U.S. Appl. No. 12/883,071, filed Sep. 15, 2010, 8 pages.
Non-Final Office Action mailed on May 13, 2011, for U.S. Appl. No. 12/883,087, filed Sep. 15, 2010, 7 pages.
Non-Final Office Action mailed on Jun. 14, 2011, for U.S. Appl. No. 12/437,374, filed May 7, 2009, 8 pages.
Non-Final Office Action mailed on Jun. 21, 2011, for U.S. Appl. No. 12/270,695, filed Nov. 13, 2008, 24 pages.
Non-Final Office Action mailed on Jul. 13, 2011, for U.S. Appl. No. 12/334,373, filed Dec. 12, 2008, 8 pages.
Non-Final Office Action mailed on Sep. 26, 2011, for U.S. Appl. No. 12/334,382, filed Dec. 12, 2008, 7 pages.
Non-Final Office Action mailed on May 11, 2012, for U.S. Appl. No. 12/883,071, filed Sep. 15, 2010, 7 pages.
Non-Final Office Action mailed on Jun. 7, 2012, for U.S. Appl. No. 12/334,395, filed Dec. 12, 2008, 7 pages.
Non-Final Office Action mailed on Oct. 18, 2012, for U.S. Appl. No. 12/541,840, filed Aug. 14, 2009, 10 pages.
Non-Final Office Action mailed on Mar. 15, 2013, for U.S. Appl. No. 12/512,855, filed Jul. 30, 2009, 10 pages.
Non-Final Office Action mailed on Sep. 12, 2013 for U.S. Appl. No. 13/341,732, filed Dec. 30, 2011, 5 pages.
Non-Final Office Action mailed on Sep. 23, 2013, for U.S. Appl. No. 12/883,087, filed Sep. 15, 2010, 7 pages.
Non-Final Office Action mailed on Feb. 27, 2014, for U.S. Appl. No. 12/270,695, filed Nov. 13, 2008, 7 pages.
Non-Final Office Action mailed on Apr. 16, 2014, for U.S. Appl. No. 12/334,395, filed Dec. 12, 2008, 9 pages.
Non-Final Office Action mailed on Jun. 12, 2014, for U.S. Appl. No. 14/082,010, filed Nov. 15, 2013, 6 pages.
Non-Final Office Action mailed on Sep. 23, 2014, for U.S. Appl. No. 13/341,732, filed Dec. 30, 2011, 13 pages.
Non-Final Office Action mailed on Mar. 20, 2015, for U.S. Appl. No. 12/883,087, filed Sep. 15, 2010, 11 pages.
Notice of Allowance mailed on Dec. 23, 2009, for U.S. Appl. No. 12/419,925, filed Apr. 7, 2009, 2 pages.
Notice of Allowance mailed on Dec. 23, 2009, for U.S. Appl. No. 12/419,943, filed Apr. 7, 2009, 2 pages.

(56) References Cited

OTHER PUBLICATIONS

Notice of Allowance mailed on Dec. 24, 2009, for U.S. Appl. No. 12/419,927, filed Apr. 7, 2009, 2 pages.
Notice of Allowance mailed on Jan. 19, 2010, for U.S. Appl. No. 12/419,930, filed Apr. 7, 2009, 2 pages.
Notice of Allowance mailed on Feb. 2, 2010, for U.S. Appl. No. 12/419,937, filed Apr. 7, 2009, 2 pages.
Notice of Allowance mailed on Mar. 18, 2011, for U.S. Appl. No. 12/258,277, filed Oct. 24, 2008, 7 pages.
Notice of Allowance mailed on Mar. 21, 2011, for U.S. Appl. No. 12/258,282, filed Oct. 24, 2008, 8 pages.
Notice of Allowance mailed on Mar. 21, 2011, for U.S. Appl. No. 12/883,059, filed Sep. 15, 2010, 10 pages.
Notice of Allowance mailed on Mar. 23, 2011, for U.S. Appl. No. 12/883,079, filed Sep. 15, 2010, 9 pages.
Notice of Allowance mailed on Mar. 25, 2011 for U.S. Appl. No. 12/883,090, filed Sep. 15, 2010, 8 pages.
Notice of Allowance mailed on Mar. 25, 2011, for U.S. Appl. No. 12/883,056, filed Sep. 15, 2010, 8 pages.
Notice of Allowance mailed on Jul. 13, 2011, for U.S. Appl. No. 11/398,342, filed Apr. 4, 2006, 7 pages.
Notice of Allowance mailed on Nov. 9, 2011, for U.S. Appl. No. 12/479,794, filed on Jun. 6, 2009, 7 pages.
Notice of Allowance mailed on Aug. 20, 2012, for U.S. Appl. No. 12/437,374, filed May 7, 2009, 8 pages.
Notice of Allowance mailed on Nov. 2, 2012, for U.S. Appl. No. 11/775,157, filed Jul. 9, 2007, 8 pages.
Notice of Allowance mailed on May 22, 2013, for U.S. Appl. No. 11/775,157, filed Jul. 9, 2007, 10 pages.
Notice of Allowance mailed on Jul. 15, 2013, for U.S. Appl. No. 12/334,382, filed Dec. 12, 2008, 9 pages.
Notice of Allowance mailed on Jul. 30, 2013, for U.S. Appl. No. 12/334,373, filed Dec. 12, 2008, 10 pages.
Notice of Allowance mailed on Sep. 19, 2013, for U.S. Appl. No. 12/883,071, filed Sep. 15, 2010, 6 pages.
Notice of Allowance mailed on Nov. 27, 2013, for U.S. Appl. No. 12/512,855, filed Jul. 30, 2009, 9 pages.
Notice of Allowance mailed on Jan. 21, 2014, for U.S. Appl. No. 12/883,071, filed Sep. 15, 2010, 6 pages.
Notice of Allowance mailed on Feb. 19, 2014, for U.S. Appl. No. 12/512,855, filed Jul. 30, 2009, 7 pages.
Notice of Allowance mailed on Apr. 8, 2014, for U.S. Appl. No. 12/541,840, filed Aug. 14, 2009, 8 pages.
Notice of Allowance (Corrected) mailed on May 29, 2014, for U.S. Appl. No. 12/512,855, filed Jul. 30, 2009, 4 pages.
Notice of Allowance mailed on Jun. 12, 2014, for U.S. Appl. No. 12/270,695, filed Nov. 13, 2008, 7 pages.
Notice of Allowance mailed on Feb. 17, 2015, for U.S. Appl. No. 14/082,010, filed Nov. 15, 2013, 7 pages.
Nuutinen, J-P. et al. (2002). "Mechanical Properties and in vitro Degradation of Bioresorbable Knitted Stents," *J. Biomater. Sci. Polymer Edn.* 13(12):1313-1323.
Nuutinen, J-P. et al. (2003). "Theoretical and Experimental Evaluation of the Radial Force of Self-Expanding Braided Bioabsorbable Stents," *J. Biomater. Sci. Polymer Edn.* 14(7):677-687.
Parviainen, M. et al. (2000). "A New Biodegradable Stent for the Pancreaticojejunal Anastomosis After Pancreaticoduodenal Resection: In Vitro Examination and Pilot Experiences in Humans," *Pancreas* 21(1):14-21.
Piskunov, S.Z. et al. (May-Jun. 1989). "Application of Drugs Based on Polymers in the Treatment of Acute and Chronic Maxillary Sinusitis," *Vestnik Otorinolaringologii* (3)33-35.
Piskunov, S. et al. (1993). "The Prolongation of Drug Action in the Treatment of Diseases of the Nose and Paranasal Sinuses," *Rhinology* 31:33-36.
Roumestan, C. et al. (2003). "Fluticasone Propionate and Mometasone Furoate Have Equivalent Transcriptional Potencies," *Clinical and Experimental Allergy* 33: 895-901.

Shikani, A.H. (Aug. 1996). "Use of Antibiotics for Expansion of the Merocel® Packing Following Endoscopic Sinus Surgery," *ENT Journal* 75(8):524-528.
Su, S-H. et al. (2003). "Expandable Bioresorbable Endovascular Stent. I. Fabrication and Properties," *Annals of Biomedical Engineering* 31:667-677.
Tamai, H. et al. (1999). "A Biodegradable Ploy-/-lactic Acid Coronary Stent in the Porcine Coronary Artery," *Journal of Interventional Cardiology* 12(6):443-450.
Thierry, B. et al. (Nov./Dec. 2003, e-pub. Oct. 7, 2003). "Bioactive Coatings of Endovascular Stents Based on Polyelectrolyte Multilayers," *Biomacromolecules* 4(6):1564-1571.
Third Party Submission under 37 CFR 1.290 submitted Oct. 11, 2014, against U.S. Appl. No. 14/081,974, filed Nov. 15, 2013, 8 pages.
Toffel, P.H. (Mar. 2001). "The Balanced Philosophy of Secure Multimodal Endoscopic Sinus Surgery with Adjunct Use of Middle Meatal Stenting and Middle Turbinate Modification," *Operative Techniques in Otolaryngology—Head and Neck Surgery* 12(1):40-45.
Vogt, F. et al. (2004, e-pub. Jul. 20, 2004). "Long-Term Assessment of a Novel Biodegradable Paclitaxel-Eluting Coronary Polylactide Stent," *European Heart Journal* 25:1330-1340.
Bolliger, C.T. et al. (1999). "Evaluation of a New Self-Expandable Silicone Stent in an Experimental Tracheal Stenosis," *Chest* 115:496-501.
Extended European Search Report dated on Jun. 18, 2015, for EP Patent Application No. 08 863 327.6, filed on Jul. 16, 2010, 8 pages.
Extended European Search Report dated on Jun. 26, 2015, for European Patent Application No. 09 803 604.9, filed on Jul. 30, 2009, 7 pages.
Final Office Action dated on Feb. 12, 2015, for U.S. Appl. No. 13/341,732, filed on Dec. 30, 2011, 8 pages.
Final Office Action dated on Oct. 20, 2015, for U.S. Appl. No. 12/883,087, filed on Sep. 15, 2010, 15 pages.
Final Office Action dated on Feb. 8, 2016, for U.S. Appl. No. 12/334,395, filed on Dec. 12, 2008, 18 pages.
Final Office Action dated on Jun. 29, 2016, for U.S. Appl. No. 14/327,100, filed on Jul. 9, 2014, 17 pages.
Final Office Action dated on Sep. 16, 2016, for U.S. Appl. No. 14/081,974, filed on Nov. 15, 2013, 12 pages.
Final Office Action dated on Sep. 20, 2016, for U.S. Appl. No. 14/550,634, filed on Nov. 21, 2014, 11 pages.
Hughes, J.P. et al. (Apr. 2004). "Use of a Ureteric Pigtail Stent as a Self-Retaining Frontal Sinus Stent." *The Journal of Larvnaoloav & Otoloav* 118:299-301.
International Search Report dated Feb. 24, 2006 for PCT Application No. PCT/US04/07828 filed Mar. 12, 2004, 1 page.
International Search Report dated on Nov. 9, 2006, for PCT Patent Application No. PCT/US2006/012484 filed on Apr. 04, 2006, 6 pages.
International Search Report dated on Mar. 19, 2008, for PCT Patent Application No. PCT/US2007/015813, filed on Jul. 10. 2007. 3 pages.
International Search Report dated on Mar. 11, 2009, for PCT Application No. PCT/US2008/86178, filed on Dec. 12, 2008, 3 pages.
Mirza, S. et al. (Dec. 2000). "A Simple and Effective Frontal Sinus Stent," *The Journal of Laryngology & Otology* 114:955-956.
Mitty, H. et al. (1988). "Experience with a New Ureteral Stent Made of a Biocompatible Copolymer," *Radiology* 168:557-559.
Non-Final Office Action dated on May 8, 2015, for U.S. Appl. No. 12/334,395, filed on Dec. 12, 2008, 11 pages.
Non-Final Office Action dated on Sep. 10, 2015, for U.S. Appl. No. 13/341,732, filed Dec. 30, 2011, 6 pages.
Non-Final Office Action dated on Nov. 12, 2015, for U.S. Appl. No. 14/327,100, filed on Jul. 9, 2014, 12 pages.
Non-Final Office Action dated on Feb. 5, 2016, for U.S. Appl. No. 12/883,087, filed on Sep. 15, 2010, 12 pages.
Non-Final Office Action dated on Feb. 5, 2016, for U.S. Appl. No. 14/081,974, filed on Nov. 15, 2013, 12 pages.
Non-Final Office Action dated on Apr. 28, 2016, for U.S. Appl. No. 14/550,634, filed on Nov. 21, 2014, 10 pages.

(56) References Cited

OTHER PUBLICATIONS

Non-Final Office Action dated on Aug. 11, 2016, for U.S. Appl. No. 12/334,395, filed on Dec. 12, 2008, 12 pages.
Notice of Allowance dated on Nov. 12, 2014, for U.S. Appl. No. 14/082,010, filed on Nov. 15, 2013, 5 pages.
Notice of Allowance dated on Nov. 18, 2016, for U.S. Appl. No. 14/298,715, filed on Jun. 6, 2014, 8 pages.
Supplementary European Search Report dated on Nov. 9, 2010, for European Patent Application No. 04 720 509.1, filed on Mar. 12, 2004, 3 pages.
Written Opinion of the International Searching Authority dated on Nov. 9, 2006, for PCT Patent Application No. PCT/US2006/012484, filed on Apr. 4, 2006, 11 pages.
Written Opinion of the International Searching Authority dated on Sep. 28, 2009, for PCT Application No. PCT/US2009/052287, filed on Jul. 30, 2009, 9 pages.
Written Opinion of the International Searching Authority dated Feb. 24, 2006 for PCT Application No. PCT/US04/07828, filed Mar. 12, 2004, 3 pages.
Written Opinion of the International Searching Authority dated on Mar. 19, 2008, for PCT Patent Application No. PCT/US2007/015813, filed on Jul. 10, 2007, 7 pages.
Written Opinion of the International Searching Authority dated on Apr. 16, 2009, for PCT Application No. PCT/US2008/86718, filed on Dec. 12, 2008, 13 pages.

\* cited by examiner

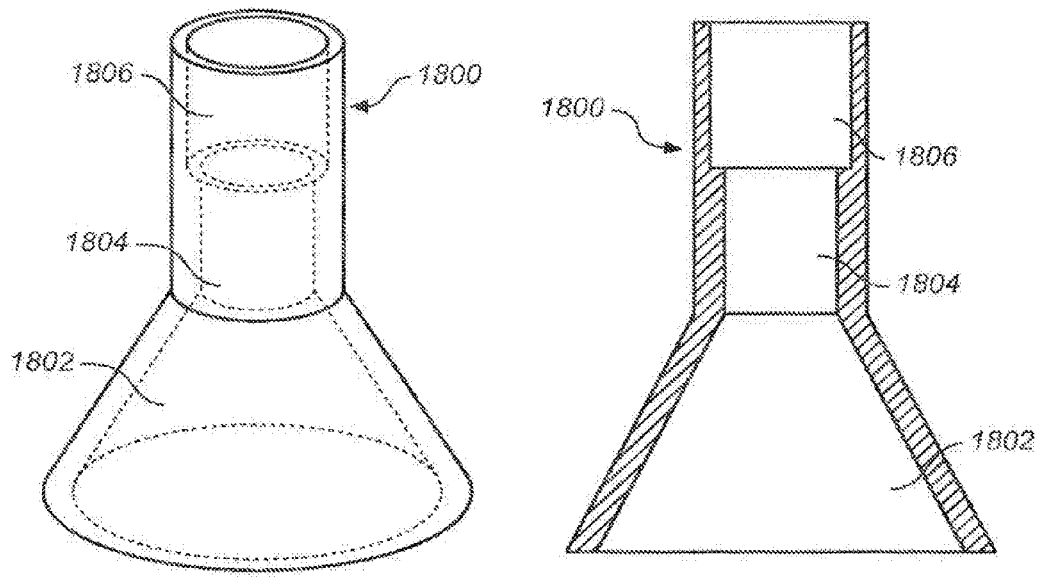
FIG. 18A    FIG. 18B
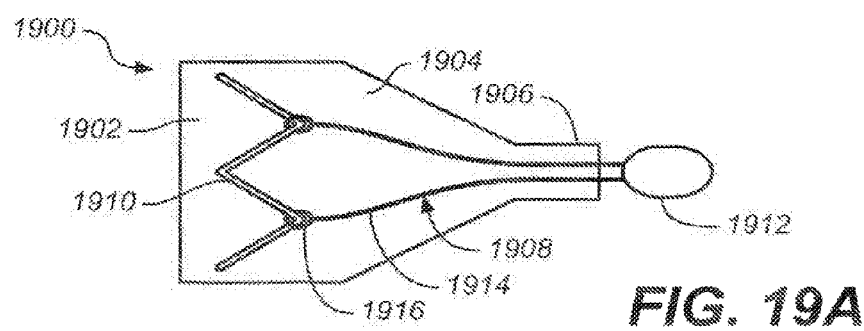
FIG. 19A
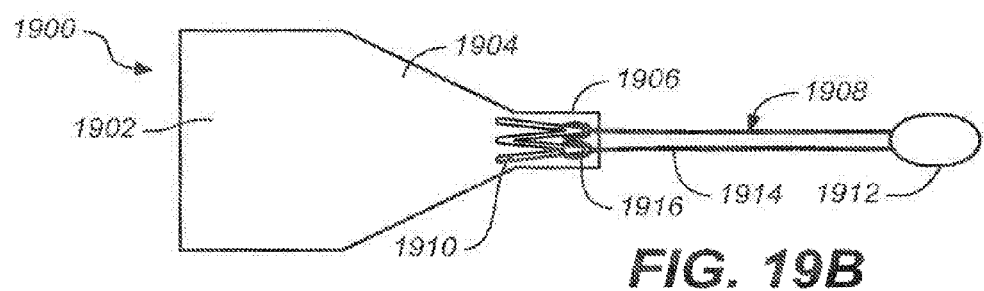
FIG. 19B

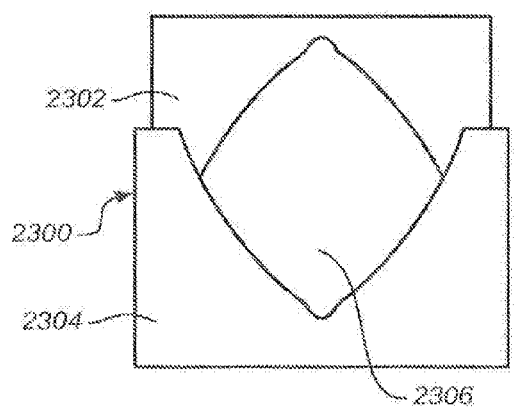
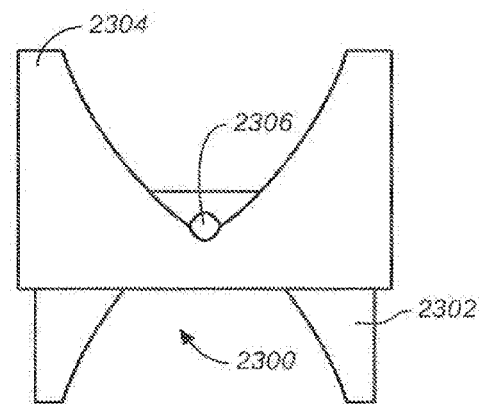
FIG. 23A
FIG. 23B
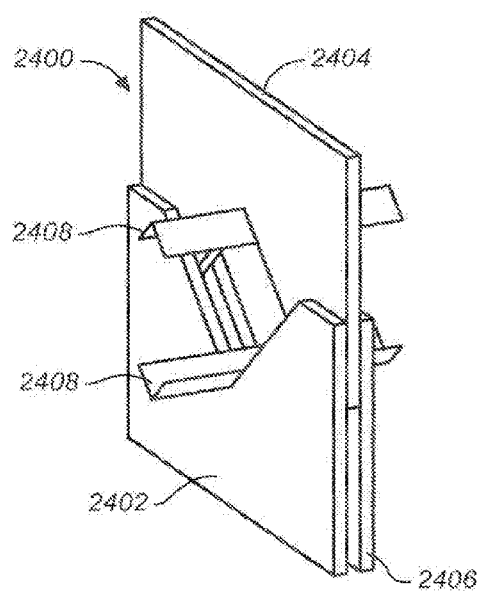
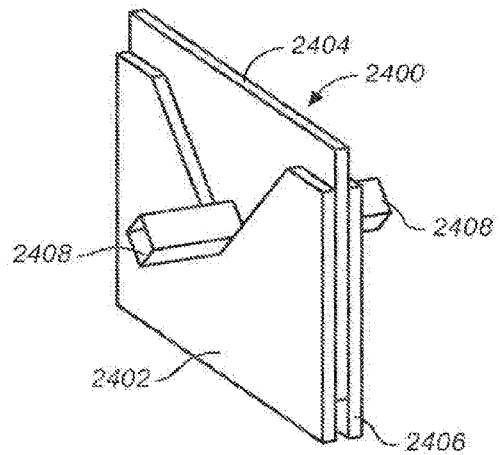
FIG. 24A
FIG. 24B

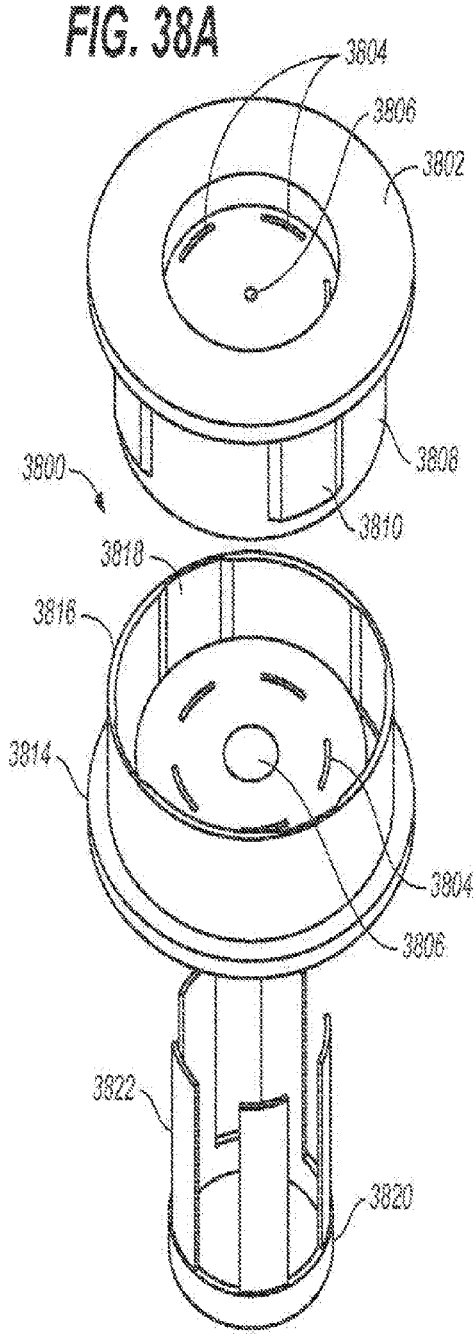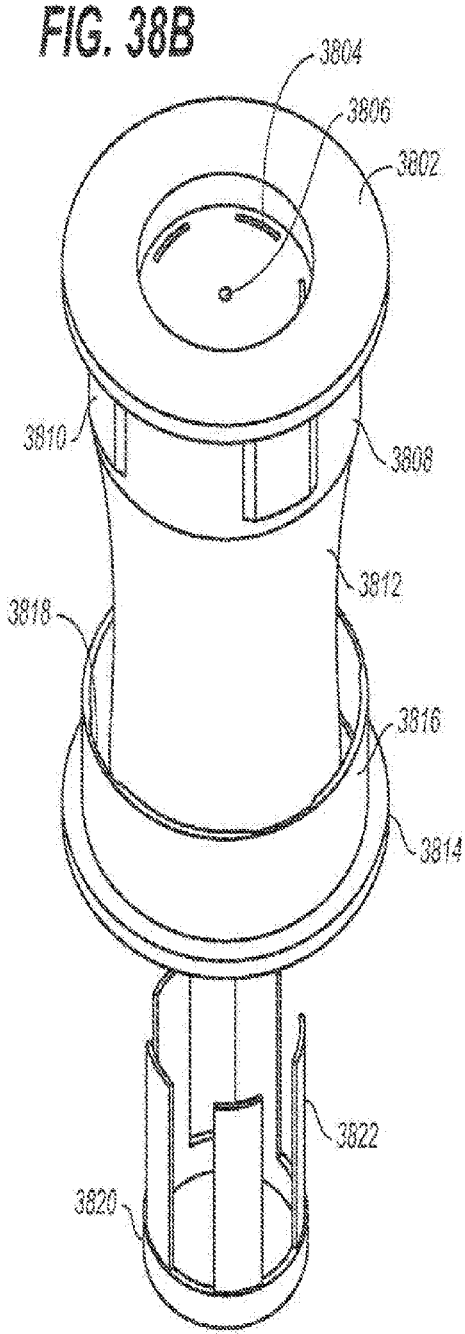

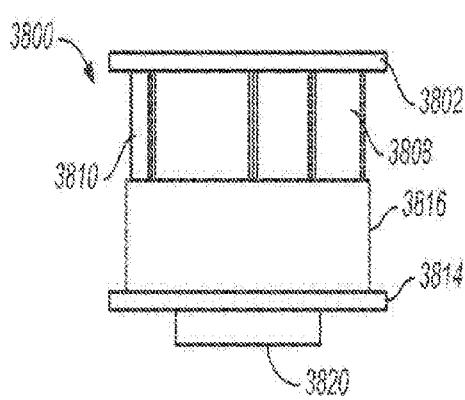
FIG. 38C
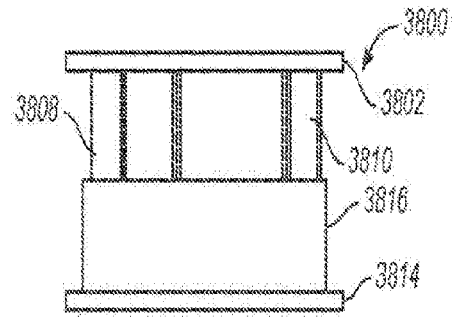
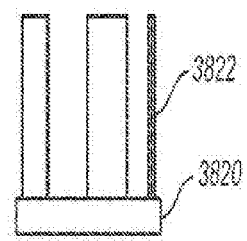
FIG. 38E
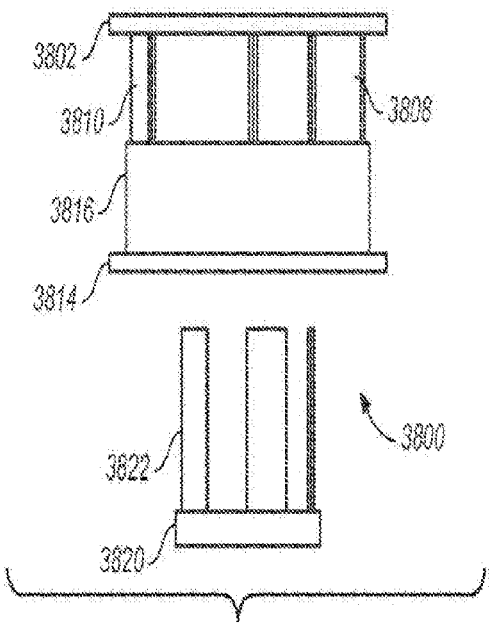
FIG. 38D
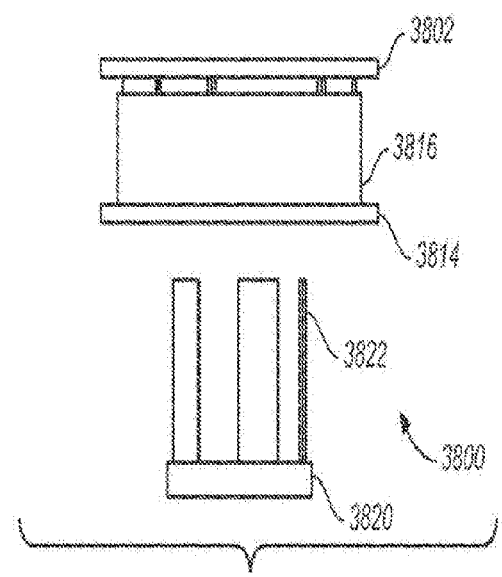
FIG. 38F

METHODS AND DEVICES FOR CRIMPING SELF-EXPANDING DEVICES

CROSS REFERENCE TO RELATED APPLICATIONS

This application is a continuation application of U.S. application Ser. No. 12/512,855, filed Jul. 30, 2009, now issued as U.S. Pat. No. 8,763,222, which claims priority to U.S. Provisional Application Ser. No. 61/085,795, filed Aug. 1, 2008, the entirety of each of which is hereby incorporated by reference in its entirety.

FIELD

The present invention relates generally to methods and devices for crimping self-expanding devices.

BACKGROUND OF THE INVENTION

There is a movement toward using minimally invasive approaches for treating conditions or diseases. Because they can be delivered in an unexpanded configuration, self-expanding devices may be useful to provide a minimally invasive way to maintain, open, or dilate bodily structures such as veins, arteries, ureters, urethras, hollow-body organs, nasal passages, sinus cavities, and the like. These self-expanding devices may serve a number of therapeutic functions, and may be used to release one or more drugs to a target location. Furthermore, self-expanding devices may be designed to degrade over time. For example, self-expanding devices may be used to provide anatomical support to one or more sinus openings or ostia following functional endoscopic sinus surgery.

In order to provide a self-expanding device to an anatomical location, generally it first must be reduced to an unexpanded configuration. There may be problems, however, with crimping a self-expanding device to an unexpanded configuration. These problems may arise from the geometry of the self-expanding device, from maintaining the sterility of the device, or from a number of other sources. Thus it may be useful to provide devices to crimp a self-expanding device to an unexpanded configuration.

BRIEF SUMMARY OF THE INVENTION

Described here are devices and methods for crimping self-expanding devices. The crimping devices described here may be useful for crimping a variety of different self-expanding devices. In some variations, the self-expanding device is biodegradable. In other variations, the self-expanding device is bio-durable. The self-expanding device may comprise, incorporate, or deliver one or more drugs or active agents, and the crimping device may be configured to be compatible with such drug or active agent so as not to destroy or limit its efficacy. In some variations, the devices described here have one or more crimping members. Generally, a crimping member is a structure that may engage a self-expanding device to reduce the self-expanding device to an unexpanded configuration from an expanded configuration. In some variations, the crimping members comprise a suture, wire, ribbon, guiding hoop, pusher, prong, holding bar, balloon, jaws, a combination thereof, or the like. Any crimping member, or combination of crimping members, may be used, as appropriate, with any of the crimping devices described here. Additionally, any crimping member may include one or more handles.

In some variations, crimping devices are described here having a crimping member, where the crimping member engages the self-expanding device to reduce the self-expanding device to an unexpanded configuration from an expanded configuration, and where the crimping device engages an applicator or storage member to hold the self-expanding device in its unexpanded configuration. The crimping devices described here may additionally include one or more holding structures configured to hold one or more self-expanding devices in their expanded configurations, or in some instances, their un-expanded configurations. The holding structure may define an aperture, but need not. The holding structure may be or comprise a hoop, canister, cage, plate, funnel, rod, sheath, wire, ribbon, ring, a combination thereof, or the like. The holding structure may be made of a single continuous component, or may be made of two or more separate components. Additionally, each component of the holding structure may be made of one material, or may be made from a combination of materials.

In some variations, the holding structure may include one or more passage units. Generally, passage units provide a structure through which a crimping member may pass into or out of a holding structure. Examples of suitable passage units include, but are not limited to, slits, slots, holes, grooves, contours, pulleys, and rollers. Additionally, the holding structure may include one or more tracks. When a holding structure includes one or more tracks, it may additionally include one or more pins that are slidably disposed in one or more of the one or more tracks.

In other variations of the devices described here, the crimping devices may have a holding structure, where the holding structure is configured to hold therein the self-expanding device in an expanded configuration, and a crimping control, where movement of the crimping control relative to the holding structure causes the crimping device to reduce the self-expanding device to an unexpanded configuration. In some variations, the crimping control rotates relative to the holding structure. The holding structure may be any holding structure, or combination of holding structures, and may include any feature or combination of features as described above. Additionally, the crimping control may include tracks. In variations in which both the holding structure and the crimping control include tracks, the crimping device may include pins that may be slidably disposed within the tracks of both the crimping control and the holding structure. In some of these variations, the tracks of the holding structure project radially from a center of the holding structure, and the tracks of the crimping control curve radially away from a center of the crimping control. In some variations, the crimping device includes one or more crimping members. The one or more crimping member may be any suitable crimping member or combination of crimping members as described above. In some of these variations, the crimping control engages one or more of the one or more crimping members.

In still other variations of the crimping devices described here, the crimping devices have a crimping portion where the crimping portion has a first end, a second end, an interior surface and a plurality of slits running between the first and second ends, where the cross-sectional area of the crimping portion decreases from the second end to the first end, and where the interior surface of the crimping portion is configured to house the self-expanding device in an expanded configuration. These variations may also include a pusher, where the pusher includes a plurality of prongs that engage one or more of the plurality of slits and where movement of the pusher from the second end of the crimping portion toward the first end of the frame compresses the self-expanding device into an unexpanded configuration. Additionally, the crimping portion may define an aperture through which the self-expanding device may be retrieved. In some variations, the crimping device may include a storage zone that is configured to releasably hold the self-expanding device in an unexpanded configuration. In other variations, the crimping device may be configured for attachment to an applicator for delivery of the self-expanding device to a target location. The crimping device may or may not be integral with, or permanently connected or coupled to a delivery applicator.

Other variations of the crimping devices described here have a first plate and a second plate, where the first plate and second plate are slidably engagable to define an aperture and where the aperture has a cross-sectional area that changes when the first plate is slid relative to the second plate. In some variations, the crimping device may include a third plate. This third plate may be fixedly attached to one or more of the other plates, or may be slidably engagable with one ore more the other plates. Additionally, the aperture defined by the plates may have a substantially symmetrical shape, but need not. In some variations, the aperture has a substantially diamond shape.

Still other variations of crimping devices are described here having a crimping portion that may be configured to reduce the self-expanding device from an expanded configuration to an unexpanded configuration, a storage zone that may be configured to house the self-expanding device in its unexpanded configuration, and an applicator engagement portion that may be configured to engage a distal end of an applicator. In some variations, the crimping device may have one or more blades or cutting structures. In other variations, the crimping device may include a funnel.

Also described here are methods for crimping a self-expanding device. Generally, any of the devices described here may be used to crimp a self-expanding device. Furthermore, any of the methods described here may be used to crimp any suitable self-expanding device, such as a biodegradable self-expanding device. In some methods, a self-expanding device may be crimped directly into the interior of a delivery device or storage member using a crimping device. In some of these methods, the crimping device is integral with the delivery device or storage member. In some of these methods, the crimping device may have a funnel. In other methods, the crimping device may have one or more crimping members. In still other methods the crimping device may define an aperture.

In other variations of the methods described here, a self-expanding device may be crimped using a crimping device and may be retrieved from the crimping device via a delivery device. In other variations, the crimped self-expanding device may be retrieved through an aperture defined by the crimping device. In some methods, the crimping device may include one or more connection members. Examples of suitable connection members include, but are not limited to sutures, ribbons, guiding hoops, pushers, balloons, combinations thereof, and the like. In other methods, the crimping device has one or more handles. In still other methods the crimping device may include a holding structure such as a hoop, or may include one or more passage units.

Still other methods for crimping a self-expanding device are described here comprising crimping a self-expanding device to an unexpanded configuration using a crimping device and maintaining the self-expanding device in its unexpanded configuration using a water-soluble component.

Also described here are methods of using a self-expanding device. Generally these methods comprise storing the self-expanding device in its expanded configuration, crimping the self-expanding device to its unexpanded configuration immediately prior to use, and delivering the self-expanding device at an anatomical location. These methods may be utilized for biodegradable self-expanding devices. In some of these methods, the expanded self-expanding device is stored in a protective container.

BRIEF DESCRIPTION OF THE DRAWINGS

FIGS. 7A and 7B are perspective views showing the crimping device engaging a self-expanding device in an expanded configuration and an unexpanded configuration, respectively. FIGS. 7C and 7D are top views showing the crimping device engaging a self-expanding device in an expanded configuration and an unexpanded configuration, respectively.

FIG. 10A is a perspective view of the entire crimping device. FIGS. 10B and 10C are cutaway views of the interior of the crimping device of FIG. 10A.

FIG. 12A is a perspective view of the crimping control. FIG. 12B is a perspective view of the entire crimping device and FIGS. 12C and 12D are bottom views of the crimping device of FIG. 12B.

FIGS. 18A-22B depict illustrative variations of suitable crimping devices described here, having crimping portions.

FIGS. 23A-24B depict illustrative variations of suitable crimping devices described here having two or more plates.

FIGS. 36A-38F show illustrative depictions of suitable variations of crimping devices having crimping tubes.

DETAILED DESCRIPTION OF THE INVENTION

Described here are devices for crimping a self-expanding device into an unexpanded configuration. Methods for crimping self-expanding devices are also described here. This self-expanding device may be biodegradable, but need not be. For example, the self-expanding devices may be bio-durable, or made of one or more bio-durable components (e.g., metals, biod-durable polymers, etc.). Furthermore, the devices and methods described here may be utilized to reduce self-expanding devices of a variety of shapes and configurations. For example, the self-expanding device may have a tubular structure, such as a coil. The self-expanding device may have a crown shape, or a substantially repeating diamond pattern. The crimping devices and methods described here may find particular utility with the self-expanding devices described in application No. 61/058,803, which is hereby incorporated by reference herein in its entirety. Additionally, the crimping devices described here may be configured to crimp multiple self-expanding devices.

Methods for crimping a self-expanding device generally involve using one of the devices described here to engage and reduce a self-expanding device from an expanded configuration to an unexpanded configuration. In some variations, the crimped self-expanding device is then transferred into a storage member, applicator or other device. In some methods, the self-expanding device may be crimped directly into a storage member, applicator, or other device. In other methods, the self-expanding device may be removed from the crimping device using a storage member, applicator, or other device (e.g., through one or more apertures or the like). In still other methods, an additional device may be used to move the crimped self-expanding device from the crimping device to a storage member, applicator, or other device. In some methods, part or all of the crimping device is disengaged from the self-expanding device following crimping.

In some instances, it may be desirable to maintain a self-expanding device in an expanded configuration until a time immediately prior to delivery (e.g., minutes, hours, or days). As such, in some methods, a self-expanding device may be stored in an expanded configuration. In some of these methods, the self-expanding device may be stored in and/or on a protective container. When a self-expanding device is going to be delivered to an anatomical location, the self-expanding device may be crimped at the site of the delivery procedure, and may be crimped prior to its delivery at the anatomical location. Because the crimping devices described here may be used to crimp a self-expanding device during a sterile procedure, it may be desirable for the crimping devices described here to be sterilizable.

Figure 1:
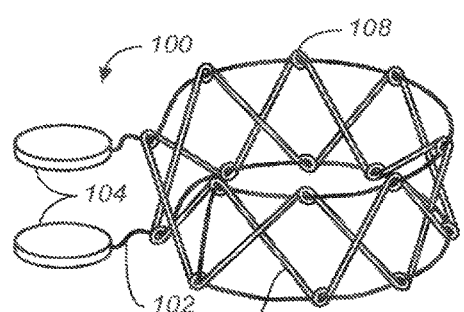
FIGS. 1-5 are illustrative depictions of suitable variations of crimping devices having one or more crimping members and one or more handles.

Some of the crimping devices described here comprise one or more crimping members. In some of these variations, the crimping devices may additionally contain one or more handles, but need not. FIG. 1 shows one suitable variation of crimping device (100), comprising crimping member (102) and handles (104), engaging self-expanding device (106) comprising loops (108). While shown in FIG. 1 as being a suture, crimping member (102) may have any suitable configuration. Generally, crimping members are configured to engage a self-expanding device to reduce the self-expanding device to an unexpanded configuration. Examples of suitable crimping members include, but are not limited to, sutures, wires, ribbons, guiding hoops, pushers, prongs, holding bars, jaws, balloons, combinations thereof, and the like.

Figure 25:
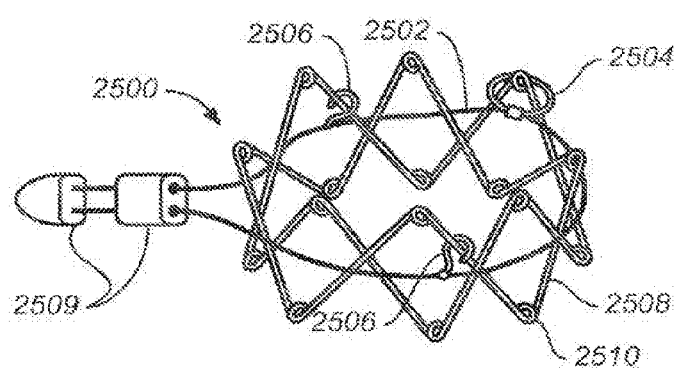
FIGS. 25-28D are illustrative depictions of suitable variations of crimping devices having one or more crimping members and one or more handles.

A crimping member may additionally include one or more structures to aid in engagement between the crimping member and the self-expanding device. For example, FIG. 25 shows one variation of device (2500) comprising handles (2509) and crimping member (2502) with ring (2504) and hooks (2506), and engaging self-expanding device (2508). Crimping member (2502) may have any combination of hooks (2506) and rings (2504). For example, crimping member may comprise zero, one, or two or more hooks (2506) and zero, one, or two or more rings (2504). Generally, hooks (2506) and rings (2504) may be placed around or through any suitable portion of self-expanding device (2508). In variations, in which self-expanding device (2508) comprises loops (2510), hooks (2506) or rings (2504) may engage one or more of these loops (2510). Although shown in FIG. 25 as being slidably disposed along crimping members (2502), rings (2504) and hooks (2506) need not be. Indeed, rings (2504) and hooks (2506) may be fixedly attached to crimping members (2502). In some variations, some of the rings (2504) and hooks (2506) may be slidably disposed along crimping members (2502) while others may be fixedly attached to crimping members (2502).

Figure 2:
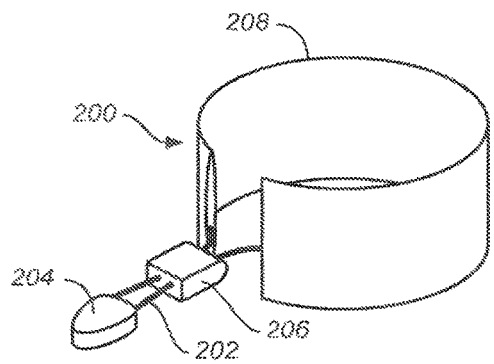
Figure 26A:
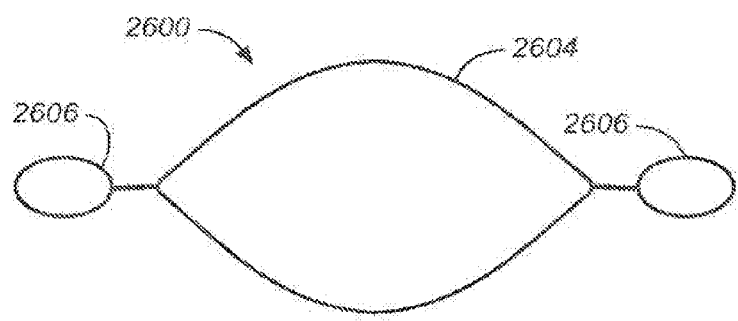
Figure 26B:
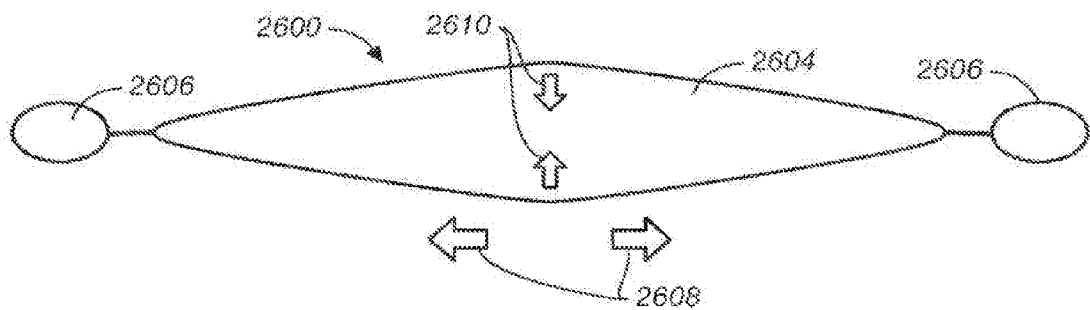

In other variations, the crimping member may include a sheath (e.g. a flexible sheath, a collapsible sheath, a sleeve, a netting or a mesh). FIG. 2 shows one such variation of crimping device (200), comprising crimping member (202), first handle (204), second handle (206), and sheath (208). This sheath (208) may aid in engagement with a self-expanding device (not shown) by increasing the surface area contact between crimping member (202) and the self-expanding device. In some variations, a crimping member may comprise a netting or mesh that may enclose a self-expanding device. For example, FIGS. 26A and 26B show one variation of crimping device (2600) comprising crimping member (2602) having netting (2604) and handles (2606). A self-expanding device (not shown), may be placed within netting (2604). As handles (2606) are pulled away from each other, netting (2604) is stretched in a horizontal direction, as indicated by first arrows (2608), which causes the width of the netting (2604) to be reduced, as indicated by second arrows (2610). This may, in turn, crimp a self-expanding device.

Figure 3:
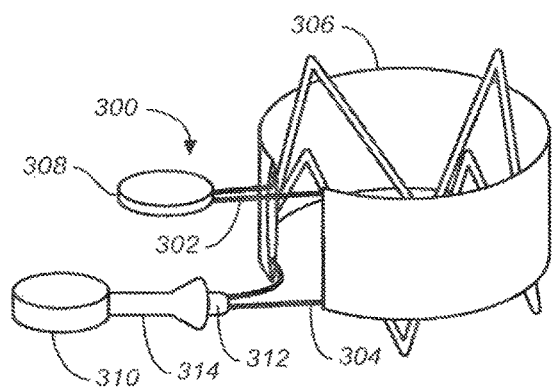

The crimping devices described here may have any number of crimping members. In some variations, the crimping device may have two or more crimping members. FIG. 3 shows one such variation of crimping device (300), comprising first crimping member (302), second crimping member (304), sheath (306), first handle (308), second handle (310) including pusher (312), and storage member (314).

In variations where the crimping device comprises handles, the crimping device may have any number of handles. Indeed, the crimping device may have three or more handles, two handles, one handle, or no handles. Furthermore, handles may have any shape or configuration, but need not have the same shape or configuration. In some variations, the handle is configured to attach to one end of one crimping member. In other variations, such as those shown in FIG. 3, the handle is configured to attach to two or more ends of crimping members. In some of these variations, the handle may attach to two or more ends of the same crimping member. In other variations, the handle may attach to one or more ends of two or more different crimping members. In still other variations, the handle is configured such that one or more ends of one or more crimping members may pass through the handle, such as the second handle (206) in FIG. 2. In some of these variations, the handle may be configured to both attach to one or more ends of one or more crimping members and allow one or more ends of one or more crimping members to pass therethrough. This may allow a user to pull a crimping member through a handle while keeping the other end of the crimping member stationary relative to the handle.

Additionally, a handle may have one or more additional features that may be useful in the operation of the crimping device. In some variations the handle may comprise a pusher, such as the second handle (310) in FIG. 3. This pusher may serve a number of functions. In variations in which the crimping device includes a storage member, as described in more detail below, the pusher may be used to eject a crimped self-expanding device from the storage member. Additionally, the pusher may be used to hold a storage member when the storage member is not engaging a self-expanding device.

Figure 4:
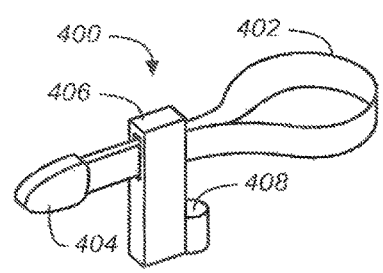

In other variations, the handle may include a structure that allows the crimping device to engage or attach to a storage member, applicator, or other device. FIG. 4 shows one such variation of crimping device (400), comprising crimping member (402), first handle (404) and second handle (406) having applicator guide (408). In the variations shown in FIG. 4, applicator guide (408) may be placed over the distal end of a storage member, applicator or other device (not shown). In other variations, applicator guide (408) may fit within, clip onto, or otherwise engage a storage member, applicator, or other device. Furthermore, while shown in FIG. 4 as being a cylindrical structure, applicator guide (408) may have any configuration that is capable of positioning a storage member, applicator or other device relative to a self-expanding device (not shown). In some variations, applicator guide may be a partial-cylinder, cone, funnel, clip, clamp, or combination thereof. Furthermore, applicator guide may have a non-circular cross-section, which may be determined by or based upon the size and shape of the applicator, storage member, or other device.

In some variations, the crimping device may include a storage member, which may, for example, hold a self-expanding device in an unexpanded configuration. FIG. 3 illustrates one variation of storage member (314). While shown in FIG. 3 as being a cylinder with a flaring end, storage member (314) may have any suitable configuration. The shape, dimensions and configuration of storage member (314) may be dependent on the shape of the crimped self-expanding device, or may be designed to hold the self-expanding device in a certain way. For example, storage member (314) may be a cylinder, a partial cylinder, a cone, a frustoconical shape, a box, a sphere, or a combination thereof. Furthermore, the storage member (314) may have any cross-sectional shape, including, but not limited to, ovals, circles, rectangles, diamonds, other polygons or shapes with irregular geometries. In some variations, the storage member may be advanced over one or more crimping members to hold a self-expanding device in an unexpanded configuration. In other variations, the storage member may be capable of attaching directly to a self-expanding device. For example, the storage member may include a clasp or clip that is capable of attaching around a crimped self-expanding device.

In some variations, the storage member may be configured to be used as an applicator to deliver a crimped self-expanding device to an anatomical location. In other variations, the storage member may be configured to attach to one or more storage members, applicators, or other devices. One or more portions of any suitable crimping device described here may be configured to be used as an applicator to deliver a crimped self-expanding device to an anatomical location, or may be configured to attach to one or more storage members, applicators, or other devices to deliver a crimped self-expanding device to an anatomical location.

Figure 5:
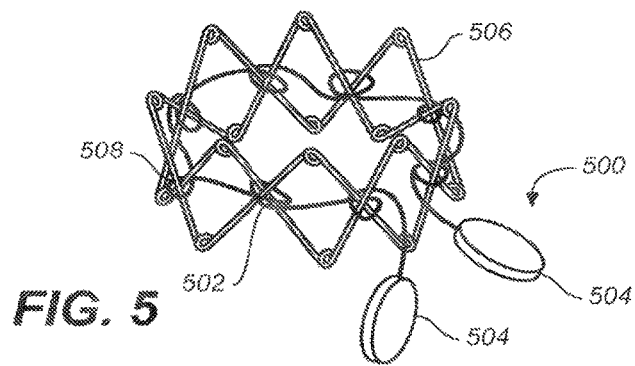

As described hereinthroughout, the crimping devices described here may engage a self-expanding device in a number of different ways. This engagement may depend on the shape, structure, or configuration of the self-expanding device, but may depend on other factors as well. In some variations, such as those shown in FIGS. 2-4, one or more crimping members wrap around the outside of the self-expanding device. In variations in which the crimping member contains hooks or rings, these hooks or rings may be attached to portions of the self-expanding device. In other variations, one or more crimping members are wound around portions of the self-expanding device. For example, FIG. 5 shows one such variation of crimping device (500) comprising crimping member (502) and handles (504), and engaging self-expanding device (506) having a substantially repeating diamond pattern comprising junctions (508). As shown in FIG. 5, crimping device may be wound around the junctions (508) of self-expanding device (506). While shown in FIG. 5 as being wound around every junction (508), crimping member (502) need not be. Indeed, crimping member (502) may be wound around all, some, or none of the junctions (508). Additionally, the crimping member may be wound around one or more different portions of the self-expanding device.

In variations in which the self-expanding device has one or more loops, the crimping device may be threaded through one or more of these loops. For example, crimping member (102) of crimping device (100) shown in FIG. 1 is threaded through loops (108) of self-expanding device (106). While shown in FIG. 1 as being threaded through each loop (108), crimping member (102) need not be. Indeed, the crimping member (102) may be threaded through all, some, or none of the loops (108).

It should be appreciated that a crimping device may engage a self-expanding device in any of the ways or combinations of the ways described above, as well as include any feature or combination of features described herein. Furthermore, in crimping devices that contain two or more crimping members, each crimping member may engage a self-expanding device in the same manner or in different manners.

Figure 6A:
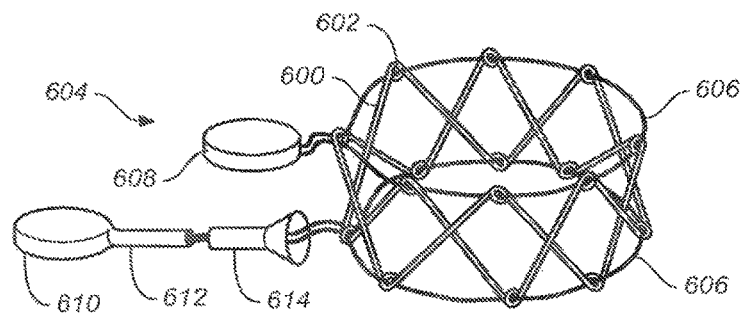
FIGS. 6A-6D depict an illustrative method of crimping a self-expanding device using a suitable variation of the crimping devices described here.
Figure 6B:
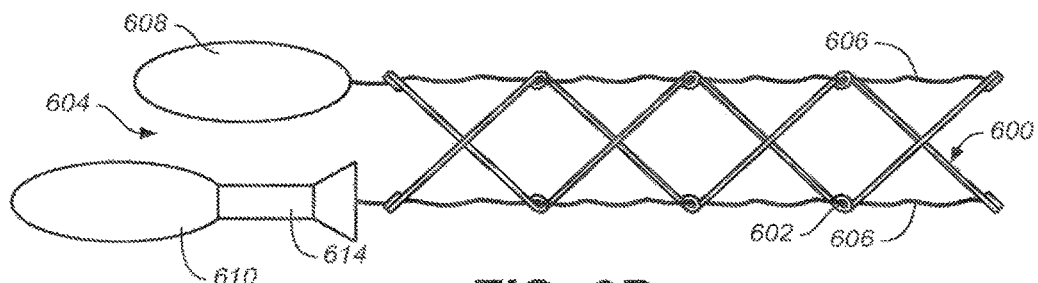
Figure 6C:
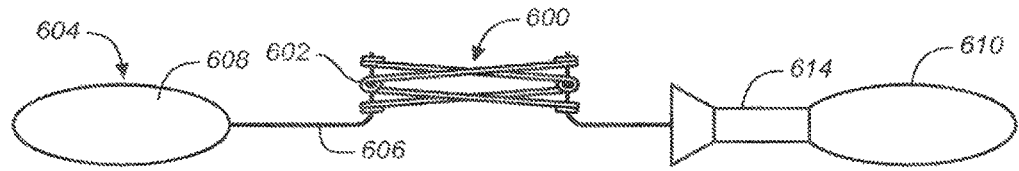

Any of the devices described above may be used to crimp a self-expanding device from an expanded configuration to an unexpanded configuration. FIGS. 6A-6D illustrate one method of crimping a self-expanding device (600) having loops (602) using crimping device (604) having crimping members (606), first handle (608), second handle (610) comprising pusher (612), and storage member (614). Initially, the crimping device (604) may engage self-expanding device (600), as shown in a perspective view in FIG. 6A and in a side view in FIG. 6B. While shown in FIGS. 6A-6D as having crimping member (606) threaded through loops (602), the crimping device (604) may engage self-expanding device (600) in any suitable manner as described above. Generally, the first (608) and second (610) handles may be pulled away from each other to reduce self-expanding device (600) to an unexpanded configuration, as shown in FIG. 6C.

Figure 6D:
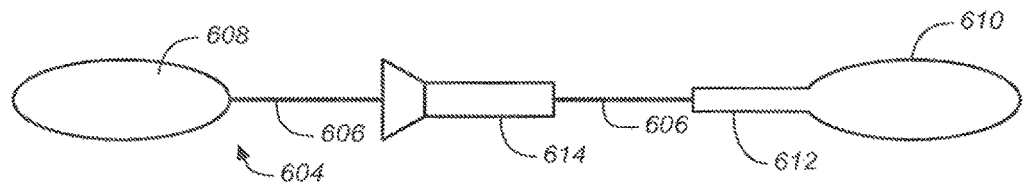

Once self-expanding device (600) has been crimped, storage member (614) may be advanced along crimping member (606) to at least partially hold self-expanding device (600) in its reduced configuration, as shown in FIG. 6D. Crimping member (600) and/or a combination of first (608) and/or second (610) handles may then be disengaged from the self-expanding device (600), but they need not be. Additionally, pusher (612) may be used to eject self-expanding device (600) from storage member (614) into an applicator or other device, or to eject self-expanding device (600) at a target location.

In other methods, the crimped self-expanding device may be transferred directly into an applicator or other device. In variations in which the crimping device includes an applicator guide, the applicator guide may be used to position the storage member, applicator, or device relative to the self-expanding device. It should be appreciated that any of the devices as described above may include any suitable combination of features described herein and may be used to reduce a self-expanding device to an unexpanded configuration.

Figure 27A:
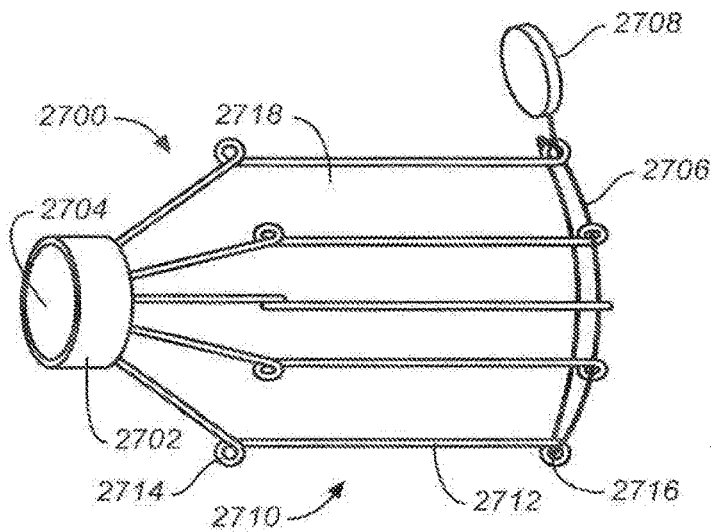
Figure 27B:
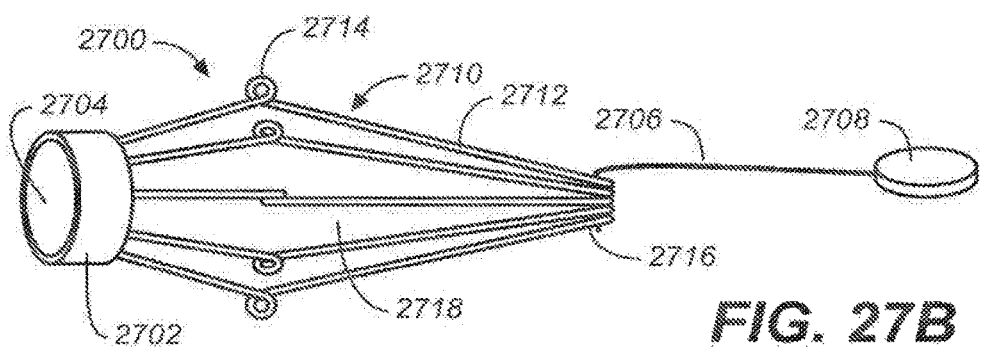
Figure 27C:
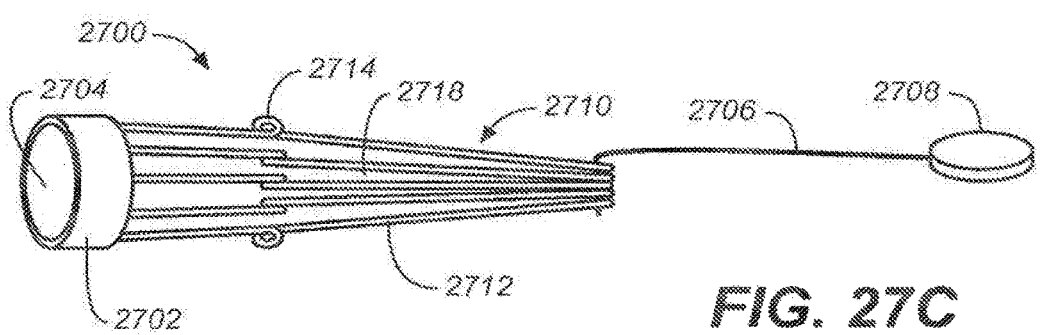
Figure 28A:
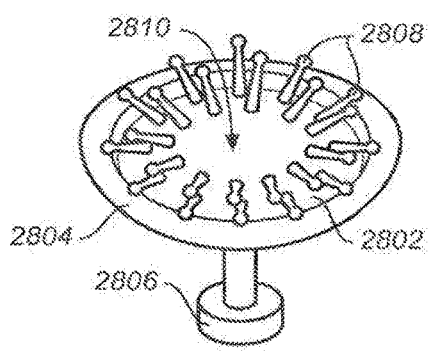
Figure 28B:
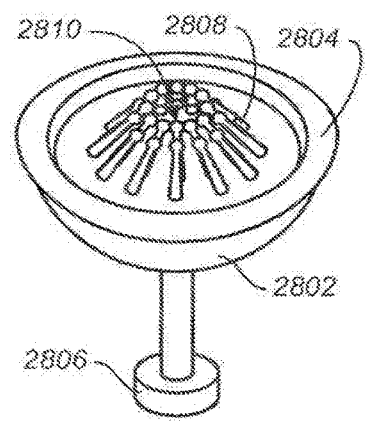
Figure 28C:
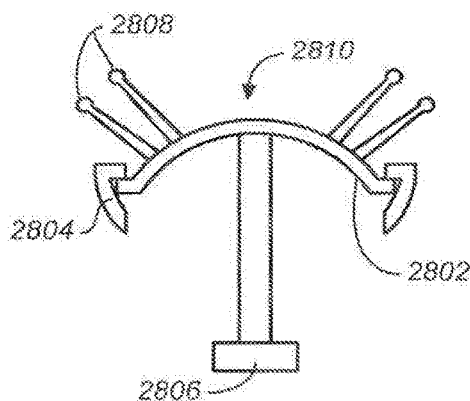
Figure 28D:
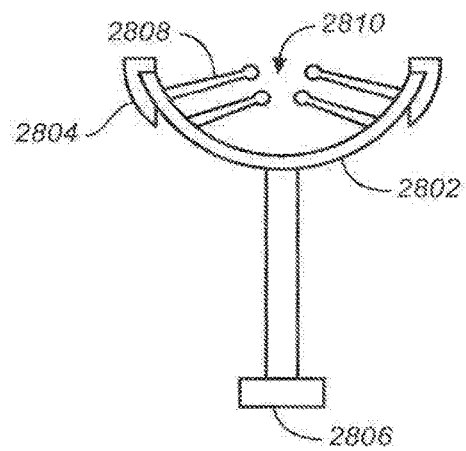

FIGS. 27A-27C show another variation of crimping device (2700) comprising cylinder (2702) defining aperture (2704), suture (2706) with handle (2708), and crimping members (2710) comprising holding bars (2712), loops (2714) and eyelets (2716). In some variations, crimping members (2710) may be rotatably attached to cylinder (2702), but need not be. Additionally, crimping members (2710) may bend at loops (2714) to define space (2718) in which a self-expanding device (not shown) may be placed, as shown in FIG. 27A. In some variations, suture (2706) may be threaded through one or more eyelets (2716). In these variations, handle (2708) may be pulled away from cylinder (2702) to close crimping members (2710) around the self-expanding device, as shown in FIG. 27B. This may hold the self-expanding device within crimping device (2700), and may additionally begin crimping the self-expanding member. Pulling handle (2708) further away from cylinder (2702) may cause the holding bars (2712) to straighten at loops (2714). This may in turn further crimp the self-expanding device. In some variations, this crimping may cause the self-expanding device to exit cylinder (2702) via aperture (2704). In other variations, the crimped self-expanding device may be removed via aperture (2704).

While shown in FIGS. 27A-27C as having loops (2714), holding bars (2712) need not. Indeed, holding bars (2712) may have hinges or joints, or may be made from a flexible material that is capable of straightening when a certain force is applied to it. Furthermore, in variations in which the holding bars (2712) have loops, hinges, or joints, they may have any number or combination of loops, hinges, and joints. Furthermore, while shown as being attached to cylinder (2702), holding bars (2712) may be attached to any suitable structure having any suitable size and shape.

FIGS. 28A-28D show another variation of crimping device (2800), comprising base (2802), rim (2804), handle (2806) and a plurality of crimping members (2808). Crimping members (2808) may be attached to base (2802), and base (2802) may in turn be attached to rim (2804) and handle (2806). Generally, base (2802) may be able to move between an open position, as shown in a perspective view in FIG. 28A, and a closed position, as shown in a perspective view in FIG. 28B. In some variations, handle (2806) may be used to move base (2802) between open and closed positions. In other variations, when the base (2802) is in an open position, crimping members (2808) are directed outward, defining space (2810). When the base (2802) is moved into the closed position, crimping members (2808) may rotate inward, decreasing the size of space (2810). To crimp a self-expanding device using crimping device (2800), self-expanding device may be placed in space (2810) when the base (2802) is in an open position, as shown in a side view in FIG. 28C. When handle (2806) moves base (2802) into a closed position, crimping members (2808) may engage self-expanding device to crimp self-expanding device to an unexpanded configuration, as shown in a side view in FIG. 28D.

Figure 29A:
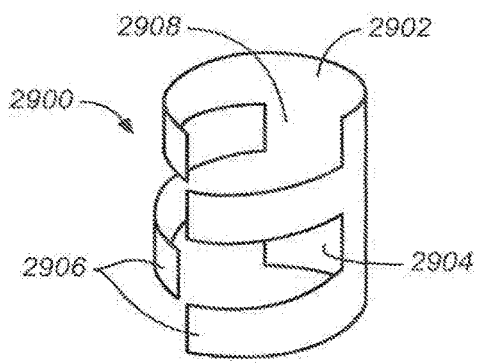
FIGS. 29A-29E depict an illustrative variation of a crimping device having one or more crimping members.
Figure 29B:
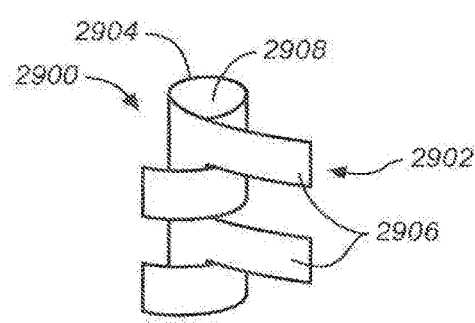
Figure 29C:
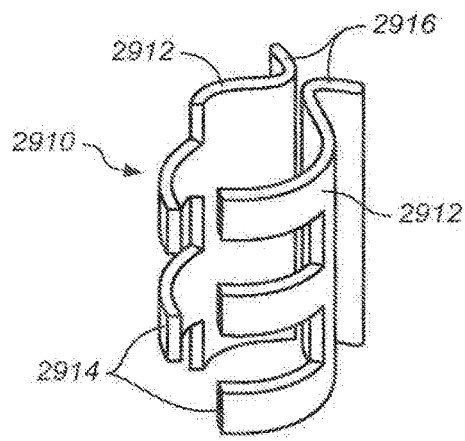

In some variations, crimping devices may comprise one or more crimping members that have one or more jaws. FIGS. 29A-29E show variations of crimping members comprising one or more jaws. More specifically, FIG. 29A shows one variation of crimping device (2900) comprising crimping member (2902) in an open position and having base portion (2904) and alternating jaws (2906). In these variations, crimping member (2902) may define a space (2908), and may be configured to change to a closed position in which alternating jaws (2906) move past each other to reduce the size of space (2908), as shown in FIG. 29B. In some variations, crimping member (2902) may be made of a material that has a natural tendency to move the crimping member (2904) to a closed position. In other variations, the crimping member (2902) may close in response to an external force. While shown in FIGS. 29A and 29B as being a single component, crimping member (2902) may be made of two or more components. For example, FIG. 29C shows one such variation of crimping member (2910) comprising hinged portions (2912), each having alternating jaws (2914) and handles (2916).

Figure 29D:
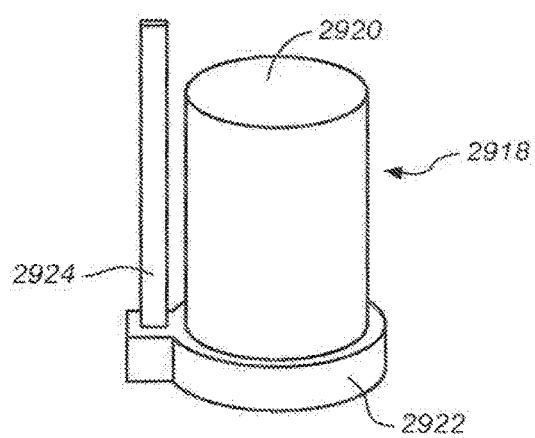
Figure 29E:
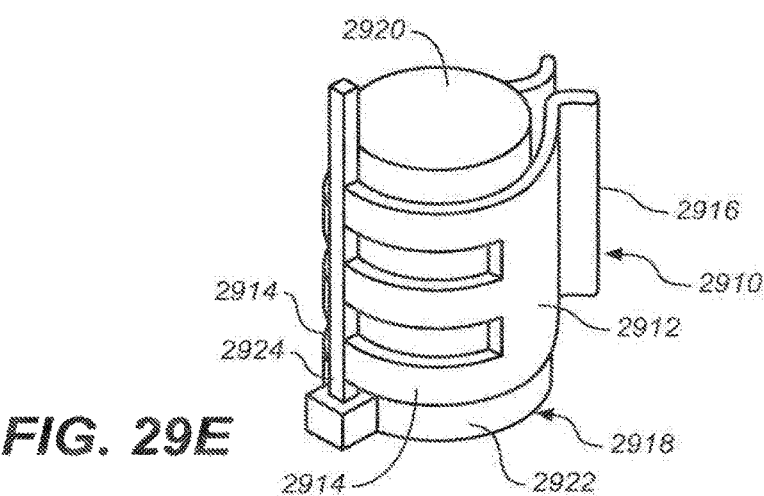

To crimp a self-expanding device (not shown) using crimping device (2900), the self-expanding device may be placed within space (2908) when crimping member (2902) is an open position. When the crimping member (2902) moves to a closed position, alternating jaws (2906) and base portion (2904) may engage the self-expanding device to crimp the self-expanding device to an unexpanded configuration. In some variations, the self-expanding device may be crimped from a storage structure. FIG. 29D shows one variation of storage structure (2918) comprising holder (2920), base (2922) and separator (2924). Generally, a self-expanding device (not shown) may be placed around holder (2920) and stored in an expanded configuration. A crimping device may then be placed around storage structure (2918). FIG. 29E shows the crimping member (2910) of FIG. 29C placed around the storage structure (2918) of FIG. 29D. Although shown in FIGS. 29D and 29E as having separator (2924), storage structure (2918) need not. In variations that do include a separator (2924), the separator (2924) may serve to hold the alternating jaws (2914) apart. The storage device (2918) may be pulled through crimping member (2910) to leave the self-expanding device within crimping member (2910). In some variations, crimping member (2910) may comprise a lip (not shown) or some other structure configured to ensure that the self-expanding device remains within crimping member (2910). As this point, the crimping member (2910) may change from an open position to a closed position in order to crimp the self-expanding device as described above.

In some variations, the crimping devices include a holding structure and one or more crimping members. In these variations, the holding structure is generally configured to hold a self-expanding device in an expanded configuration, although it is noted that in other configurations the holding structure may be generally configured to hold the self-expanding device in an un-expanded configuration. One or more crimping members may then engage the self-expanding device to reduce the self-expanding device to an unexpanded configuration. The self-expanding device may either be crimped directly into a storage member, applicator, or other device, or may be transferred following crimping to a storage member, applicator, or other device.

Figure 7A:
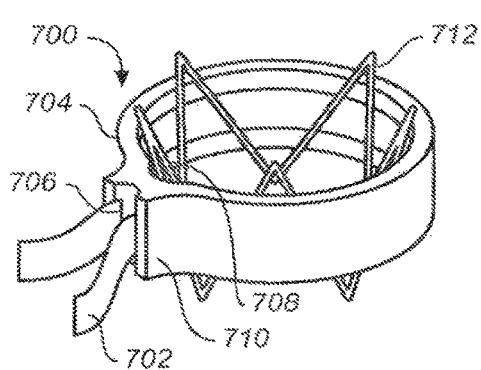
FIGS. 7A-7D are illustrative depictions of a suitable crimping device having a holding structure and a crimping member.
Figure 7B:
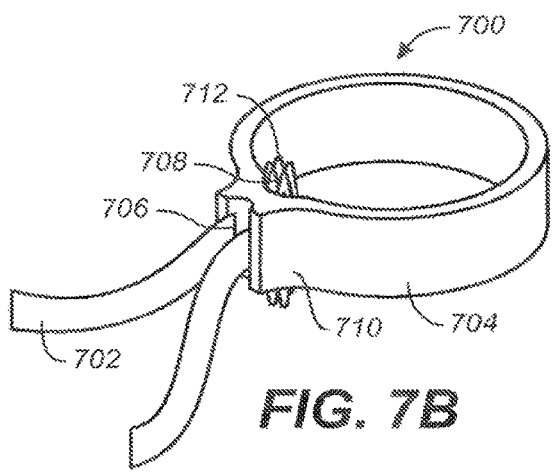
Figure 7C:
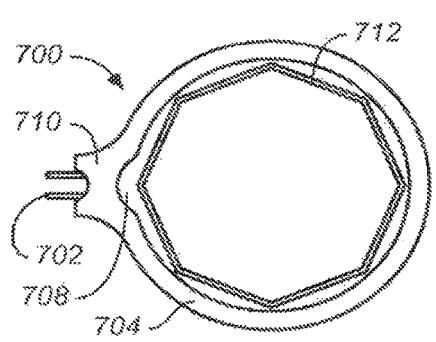
Figure 7D:
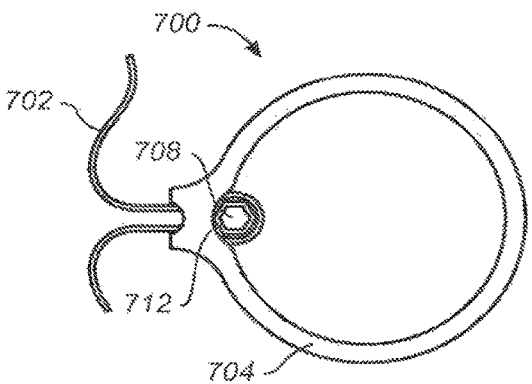

FIGS. 7A-7D illustrate one such variation of crimping device (700), comprising crimping member (702) and holding structure (704). As shown in FIGS. 7A-7D, holding structure (700) includes passage units (706), shaping portion (708), and grips (710). Also shown there is self-expanding device (712). FIG. 7A shows a perspective view and FIG. 7C shows a top view of crimping device (700) holding self-expanding device (712) in an expanded configuration. Crimping member (702) may then engage self-expanding device (712) to reduce self-expanding device (712) to an unexpanded configuration, as shown in a perspective view in FIG. 7B and in a top view in FIG. 7D.

While shown in FIGS. 7A-7D as being a hoop, holding structure (704) may be any suitable structure. Examples of suitable holding structures include, but are not limited to, hoops, canisters, cages, rods, and plates defining one or more apertures. The holding structures may be made of one or more separate pieces. Furthermore, the holding structures may have any suitable dimensions, shapes, or configurations. For example, while the hoop shown in FIGS. 7A-7D has a generally circular shape, the holding structure may define any suitable shape. Indeed, the holding structure may have an irregular shape or one that approximates an oval, a triangle, a rectangle, a polygon or the like. This shape may be determined by or may be based on the shape of the self-expanding device in its expanded configuration, but need not be. In some variations, the size and/or shape of the holding structure may be adjusted or adjustable to accept self-expanding devices of different sizes. Furthermore, although the hoop in FIGS. 7A-7D is shown as having a height less than that of the self-expanding device, the holding structure may have any suitable height. In some variations, the holding structure has a larger height than the height of the self-expanding device. In still other variations, the height of the holding structure may vary throughout the crimping device. In addition, the holding structure may include one or more additional features to help maintain the self-expanding device in a desired configuration (whether expanded or un-expanded), e.g., rings (stationary or slidable), wires, ribbons, hoops, sheaths (stationary or slidable), pushers, and the like.

Furthermore, these crimping devices may include any suitable crimping member or combination of crimping members as described above. The crimping members may also contain any feature or combination of features as described above. While shown in FIGS. 7A-7D as having one crimping member, the crimping device may incorporate any number of crimping members. Indeed, the crimping device may contain two or more crimping members. For example, in some variations the crimping device may contain two sutures encased within a sheath, similar to the crimping members shown in FIG. 3. In other variations, the crimping device may contain a plurality of crimping members, wherein each crimping member has a hook that may be used to engage the self-expanding device.

The crimping device may have any number of handles. These handles may have any shape or configuration as described above, and may be attached to any, all, or none of the crimping members. Furthermore, the holding structure may have one or more handles or grips. These handles or grips may have any suitable shape or configuration.

As described hereinthroughout, the crimping device may engage a self-expanding device in a number of different ways. This engagement may depend on the shape, structure, or configuration of the self-expanding device. In some variations, the crimping member may wrap around the self-expanding device and sit between the self-expanding device and the holding structure, as illustrated by crimping device (700) shown in FIGS. 7A-7D. In other variations, one or more crimping members may be wound around one or more portions of the self-expanding device. In variations in which one or more of the crimping members include hooks or rings, the hooks or rings may be attached or affixed to the self-expanding device. In variations in which the self-expanding device has one or more loops, one or more crimping devices may be threaded through all, some, or none of the loops. In variations in which one or more of the crimping members are balloons or pushers, the crimping member may push against the outer surface of the self-expanding device.

Furthermore, the crimping members may engage a holding structure in a number of ways. In some variations, one or more ends of one or more crimping members are attached to the holding structure. In other variations, one or more ends of one or more crimping members pass through the holding structure via one or more passage units. By moving a portion of a crimping member through a passage unit, a user may control the amount of engagement between the crimping member and a self-expanding device. This may, in turn, control the amount of crimping of the self-expanding device. For example, in crimping device (700) shown in FIGS. 7C and 7D, pulling the ends of crimping member (702) through passage units (706) reduces the amount of crimping member (702) that resides within holding structure (700), which in turn causes crimping member (702) to pull against self-expanding device (712).

The passage units may be any suitable structure that is capable of allowing at least a portion of a crimping member to pass through at least a portion of a holding structure. Examples of suitable passage units include, but are not limited to slits, slots, holes, grooves, contours, pulleys, and rollers. Passage units may have any suitable shape and dimension. In some variations, the size and shape of the passage units may be determined by the dimensions of the crimping member. Additionally, passage units may be sized and shaped to accept one or more portions of one or more crimping members. As such, when a crimping device contains passage units, each crimping member of that crimping device may pass through all, some, or none of the passage units. For example, in some variations, such as the one shown in FIGS. 7A & 7B, each end of a crimping member passes through a different passage unit. In other variations, both ends of a crimping member pass through the same passage unit. In still other variations, one end of a crimping member is attached to the interior of the holding structure, and the other end passes through a passage unit.

In some instances, it may be desirable to limit the amount that a self-expanding device is crimped. Thus, the crimping device may include one or more features that are designed to limit a device's crimping. In some variations, one or more of the crimping members may contain a visual indicator. In these variations, one or more crimping members may have color-coded regions or other markers. In variations in which crimping occurs by pulling a crimping member through a holding structure, that crimping device may be configured such that when sufficient crimping has occurred, the visual indicator becomes visible outside of the holding structure, signaling the user to stop crimping. In variations in which crimping occurs by pushing a crimping member into a holding structure, the crimping device may be configured such that when sufficient crimping has occurred, the visual indicator ceases to be visible outside of the holding structure.

In other variations, the crimping member may contain one or more stops or other features that are unable to pass through a passage unit, and thus limit the ability of the crimping member to pass either into or out of the holding structure. The crimping member may be configured such that when the device has been sufficiently crimped, the stops engage the passage unit and prevent any further crimping. Examples of suitable stops include studs, rings, and knots that are attached to a crimping member.

Figure 30A:
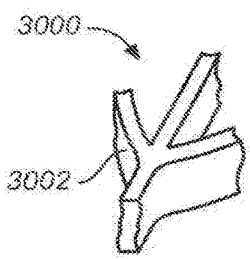
FIGS. 30A-33 depict illustrative variations of additional features that may be included in any of the crimping device described here.
Figure 30B:
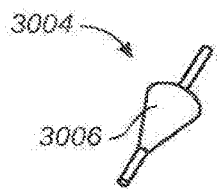
Figure 30C:
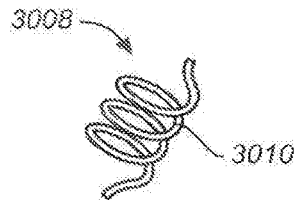

In other instances it may be desirable to prevent the self-expanding device from re-expanding once it has been reduced to an unexpanded configuration. Thus, the crimping device may include one or more features that allow a crimping member to pass through the hoop in one direction, but not the other direction. In some variations, one or more crimping members may have such a feature. Indeed, FIGS. 30A-30C show variations of crimping members having direction-limiting features. FIG. 30A shows one variation crimping member (3000) comprising flaring flaps (3002). Crimping member (3000) may comprise any number of flaring flaps (3002), and these flaring flaps (3002) may be disposed along any portion or portions of crimping member (3000). FIG. 30B shows another variation of crimping member (3004) comprising a tapered stud (3006). Crimping member (3004) may comprise any number of tapered studs (3006), and these tapered studs (3006) may be disposed along any portion or portions of crimping member (3004). FIG. 30C shows still another variation of crimping member (3008) comprising coil (3010). Coil (3010) may resist movement through a passage unit (not shown), but may temporarily deform and pass through a passage unit if pushed or pulled with enough force. On the other side of the passage unit, coil (3010) may return to its original shape, resisting a return trip through the passage unit. The coil (3010) and passage unit may be configured such that an operator-provided force is sufficient to move coil (3010) through a passage unit, but any restorative force provided by a crimped self-expanding device is insufficient to return the coil through the passage unit. Examples of suitable coil materials include, but are not limited to, shape memory materials such as nickel-titanium alloys. It should be appreciated that a crimping member may include any combination of flaring flaps, tapered studs, coils, and other features that allow for unidirectional passage of a crimping member through a passage unit.

Figure 31:
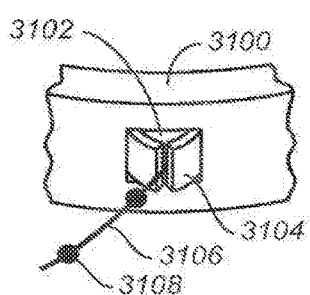
Figure 32:
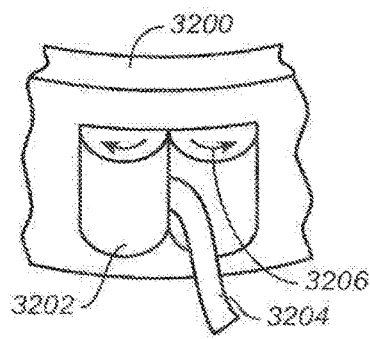

In other variations, the passage unit may contain one or more features for allowing unidirectional movement of a crimping member therethrough. For example, the passage unit may contain semi-rigid flaps. FIG. 31 shows one such variation of holding structure (3100) comprising passage unit (3102) having flaps (3104). Also shown there is crimping member (3106) comprising studs (3108). While shown in FIG. 31 as being angled outward, flaps (3104) need not be. Additionally, while shown in FIG. 31 as having studs (3108), crimping member (3106) may comprise ribs or other protrusions configured to pass through the flaps when the crimping member is pulled or pushed by a user and resist the restorative force provided by the crimped self-expanding device. In variations in which the passage unit contains rollers or pulleys, the rollers or pulleys may be configured to rotate in only one direction. FIG. 32 shows one such variation of holding structure (3200) comprising rollers (3202). Also shown there is crimping member (3204). In these variations, when a crimping member (3204) is pulled through holding structure (3200) using rollers (3202), rollers (3202) rotate in the direction indicated by arrows (3206). When crimping member (3204) is no longer being pulled, rollers (3202) hold crimping member (3204) in place against any restorative forces provided by a self-expanding device (not shown). Similarly, rollers (3202) may be configured to allow a crimping member (3204) to be pushed or pulled into holding structure (3200) and resist movement out of the holding structure (3200).

Figure 33:
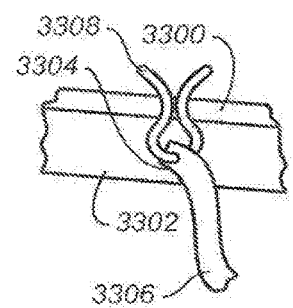

In still other variations, the crimping device may include a clamping or clasping structure configured to hold one or more crimping members in place relative to the holding structure. This clamping structure may be unable to pass through a passage unit in the holding structure, and may be attachable to a crimping member. In these variations, the clamping structure may be attached to a portion of a crimping member that has just passed through a passage unit, thereby preventing that portion from returning back through the passage unit. The clamping structure may be configured to reversibly attach to the crimping member, such that the crimping member may be later released. FIG. 33 show one such variation of crimping device (3300) comprising holding structure (3302) with passage unit (3304), crimping member (3306), and clamp (3308). Clamp (3308) may be attached to crimping member (3304) to prevent it from being pulled back through passage unit (3304), as shown in FIG. 33. Clamp (3308) may then be removed from crimping member (3304), thereby freeing crimping member (3304) to pass through passage unit (3304).

Figure 8:
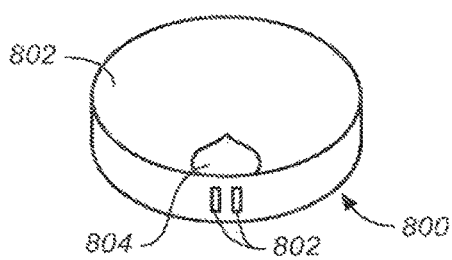
FIGS. 8-9 are illustrative depictions of suitable variations of holding structures.

The holding structure may define one or more apertures through which a crimped self-expanding device may be retrieved. FIG. 8 shows one such variation of holding structure (800) comprising canister (802) having passage structures (802) and defining aperture (804). Although shown in FIG. 8 as being located near one edge of holding structure (800), aperture (804) may be located anywhere in the holding structure (800). Indeed, in some variations the aperture may be located at the center of the holding structure. Furthermore, aperture may define any cross-sectional opening of any suitable shape. Examples of suitable shapes include, but are not limited to, circles, ovals, triangles, rectangles, other polygons, or shapes with irregular geometry. In some instances, this shape may be dependent on the self-expanding device or the storage member, applicator, or other device that may be used to retrieve the crimped self-expanding device.

Figure 9:
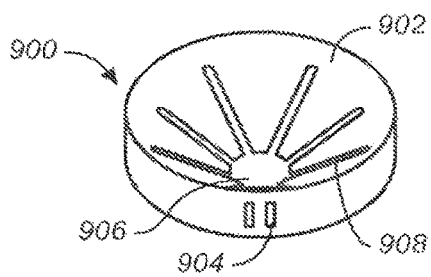

Additionally, the holding structure may comprise one or more tracks. FIG. 9 illustrates one variation of holding structure (900) comprising canister (902) having passage units (904) and defining aperture (906) and tracks (908). Tracks (908) may serve multiple functions in the operation of the crimping devices described here. In some variations, portions of a self-expanding device may pass at least partially through one or more tracks. As the self-expanding device is reduced into an unexpanded configuration, the tracks may help guide the self-expanding device along a certain path or pattern during crimping. In other variations, the crimping device includes one or more pins or bars. In some of these variations, the pins may be slidably disposed within one or more tracks in a holding structure, and the tracks may control the path of movement of the pins through the tracks. These pins may be used to aid in crimping a self-expanding device.

Tracks (908) may be located anywhere on or in holding structure (900). Although shown in FIG. 9 as being contiguous with aperture (906), tracks (908) may be non-contiguous with aperture (906). In some variations, some of tracks (908)

may be contiguous with aperture (906) while other tracks (908) may be non-contiguous with aperture (906). In variations of crimping devices that include pins, as described below, having tracks separate from an aperture may assist in preventing the pins from exiting a holding structure through that aperture. Additionally, while shown in FIG. 9 as being straight, tracks (908) need not be. Indeed, tracks may be curved, zigzagging, or may not follow a set pattern. The tracks may have a constant width or may have a varying width.

Figure 10A:
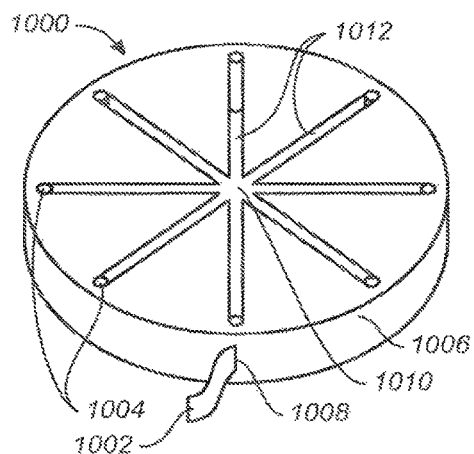
FIGS. 10A-10C depict an illustrative variation of a crimping device having a holding structure and a crimping member.
Figure 10B:
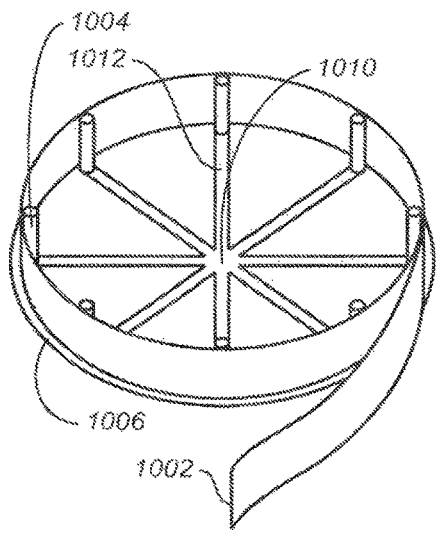
Figure 10C:
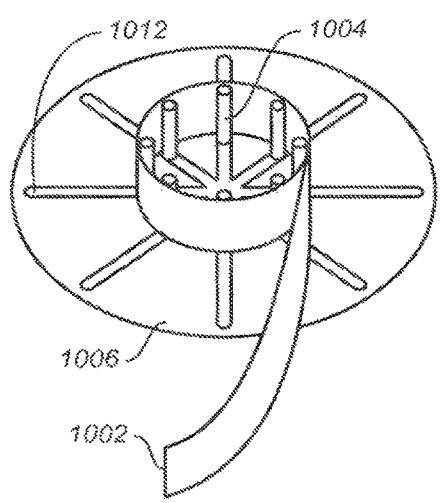

FIGS. 10A-10C illustrate one variation of crimping device (1000). Shown in FIG. 10A is a perspective view of crimping device (1000) comprising crimping member (1002), pins (1004), and holding structure (1006) having passage unit (1008) and defining aperture (1010) and tracks (1012). In this variation, pins (1004) are slidably disposed within tracks (1012). FIG. 10B shows a cutaway view of holding structure (1006). As shown in FIG. 10B, crimping member (1002) is wrapped around pins (1004). One end of crimping member (1002) exits holding structure (1006) via passage unit (1008) while the other end of crimping member (1002) is attached to one of the pins (1004). As the end of crimping member (1002) is pulled through passage unit (1008), the pins (1004) are pulled by crimping member (1002) toward the center of holding structure (1006), as shown in FIG. 10C. As the pins (1004) move toward the center of holding structure (1006), the pins may cooperate with crimping member (1002) to crimp a self-expanding device (not shown) placed inside holding structure (1006).

Figure 11:
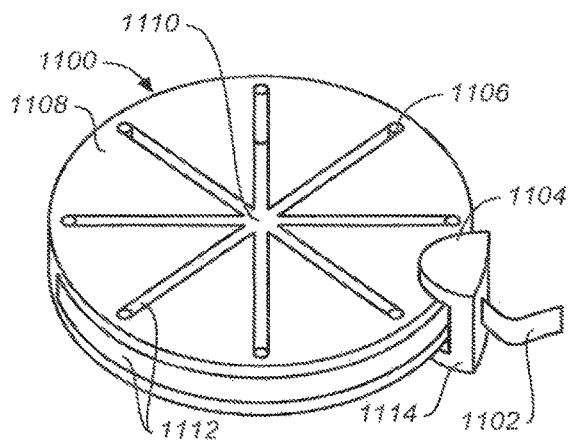
FIG. 11 is an illustrative depiction of a suitable variation of a crimping device having one or more crimping controls.

The crimping device may also include one or more crimping controls that are configured such that movement of crimping control relative to a holding structure causes the crimping device to reduce the self-expanding device to an unexpanded configuration. Examples of suitable crimping controls include, but are not limited to, ribbon pulls, cranks, winders and knobs. FIG. 11 shows one such example of crimping device (1100) comprising crimping member (1102), crimping control (1104), pins (1106), and holding structure (1108) defining aperture (1110) and tracks (1112). In FIG. 11, crimping control (1104) is a ribbon pull (1114). Generally, ribbon pull (1114) may be able to rotate around the body of holding structure (1108), and may engage crimping member (1102). In some variations, such as that shown in FIG. 11, the ribbon pull (1114) is at least partially disposed within a track (1112) defined by the holding structure (1112). Generally, when ribbon pull (1114) rotates around the body of holding structure (1108), crimping member (1102) is pulled around pins (1106) causing the pins to slide along tracks (1112), as shown in FIGS. 10B and 10C.

Figure 12A:
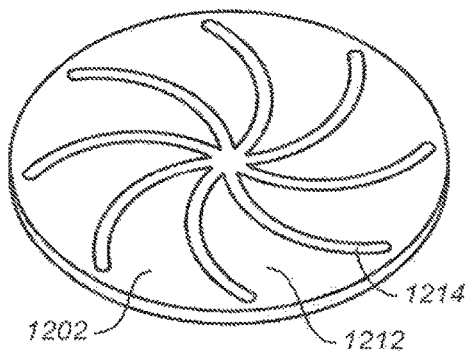
FIGS. 12A-12D show another variation of a crimping device having one or more crimping controls.
Figure 12B:
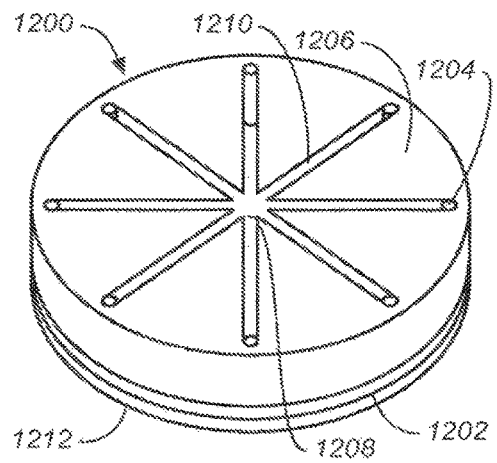
Figure 12C:
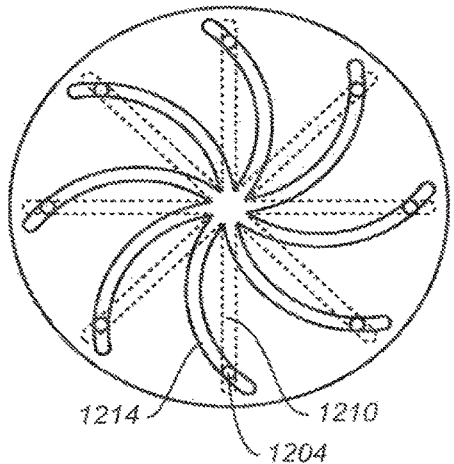
Figure 12D:
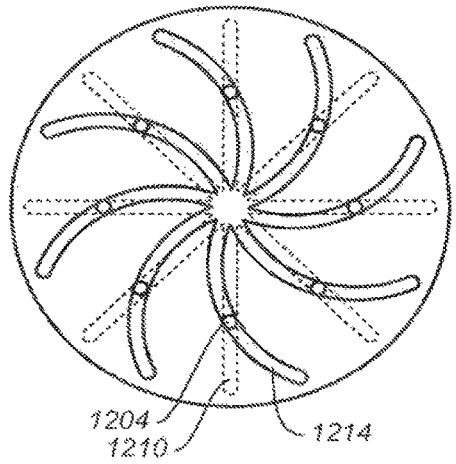

FIGS. 12A-12D show another variation of crimping device (1200) comprising crimping control (1202), pins (1204), and holding structure (1206) defining aperture (1208) and tracks (1210). FIG. 12A shows a perspective view of crimping control (1200) comprising plate (1212) with crimping tracks (1214). When crimping device (1200) is assembled, pins (1204) may be slidably disposed in both tracks (1210) of holding structure (1206) and crimping tracks (1214) of crimping control (1202), as shown in FIG. 12B. Generally, tracks (1210) of holding structure (1206) and crimping tracks (1214) of crimping control (1202) are configured such that rotation of the crimping control (1202) relative to holding structure (1206) causes the pins (1204) to slide in tracks (1210) and crimping tracks (1214). For example, as shown in FIGS. 12A-12D, tracks (1210) of holding structure (1206) may radiate away from aperture (1208) in straight lines, while crimping tracks (1214) of crimping control (1202) may radiate away from aperture (1208) in curved lines. FIGS. 12C & 12D show bottom views of pins (1204) disposed within tracks (1210) and crimping tracks (1214). Pins (1204) may fit within sections of overlap between tracks (1210) and crimping tracks (1214), and as the sections of overlap move, so do the pins (1204). As pins (1204) are moved closer together, as shown in FIG. 12D, the pins (1204) may crimp a self-expanding device (not shown).

Figure 34A:
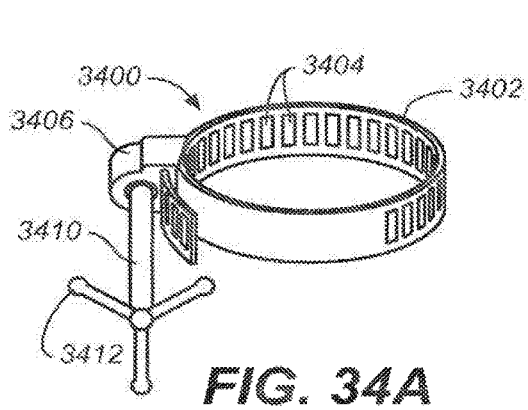
FIGS. 34A-34C show another variation of a crimping device having one or more crimping controls.
Figure 34B:
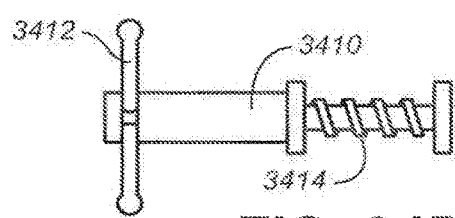
Figure 34C:

FIGS. 34A-34C illustrate another variation of crimping device (3400) comprising holding structure (3402) having slots (3404) and casing (3406). Also shown there is crimping control (3408) comprising winder (3410) having handle (3412) and threading (3414). In these variations, holding structure (3402) may be a hoop capable of assuming different shapes. FIG. 34A shows a perspective view of crimping device (3400). FIG. 34B shows a side view of winder (3410) of crimping device (3400), and FIG. 34C shows a side view of a portion of the holding structure (3402) of crimping device (3400). Generally, a portion of winder (3410) may be configured to be placed and held within casing (3406). Additionally, a portion of holding structure (3402) may pass through casing (3406), and the slots (3404) of holding structure (3402) may engage threading (3414). As winder (3410) is rotated relative to holding structure (3402), this engagement may cause a portion of holding structure (3402) to pass through casing (3406), thereby either reducing or increasing the size of the space (3416) defined by holding structure (3402). If a self-expanding device (not shown) is placed within space (3416), rotation of winder (3410) may cause holding structure (3402) to crimp the self-expanding device.

Figure 13:
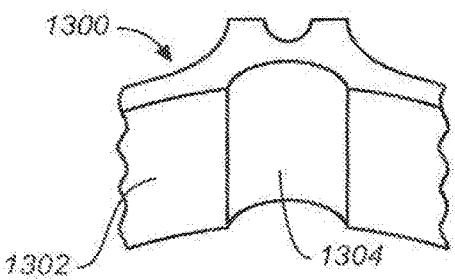
FIGS. 13-17 depict illustrative variations of additional features that may be included in any of the crimping devices described here.

The crimping device may contain a number of structures or features that may provide utility in crimping a self-expanding device. In some variations, as shown in FIG. 13, crimping device (1300) includes a holding structure (1302) that has a shaping portion (1304). Shaping portion (1304) may help to hold a self-expanding device in a certain shape when in its unexpanded configuration. Although shown in FIG. 13 as being a half-circle, the shaping portion (1304) may be any suitable shape. Indeed, shaping portion (1304) may be rectangular or triangular in shape. In variations in which the holding structure (1302) contains passage units (not shown), one or more of the passage units may be placed within shaping portion (1304), but need not be.

Figure 14:
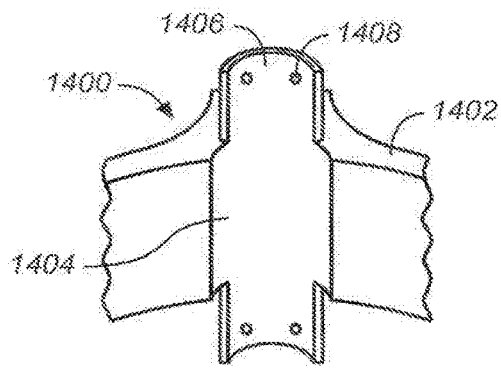

FIG. 14 shows one variation of crimping device (1400) comprising holding structure (1402) with shaping portion (1404) and applicator guides (1406) with passage units (1408). Applicator guides (1406) may serve a number of purposes. In some instances, applicator guides (1406) may be used to guide a storage member, applicator or other device (not shown) into a position to either enclose or to receive a crimped self-expanding device (not shown). While shown in FIG. 14 as having two applicator guides (1406), holding structure (1402) may have any number of applicator guides (1406). Additionally, while shown in FIG. 14 as having passage units (1408), applicator guides (1406) need not. Applicator guides (1406) with passage units (1408) may find particular utility in instances where a self-expanding device has a height greater than that of the holding structure (1402). In some of these variations, the applicator guide (1406) may function as a shaping portion, as described above.

Figure 15:
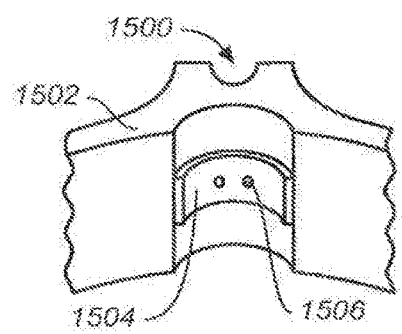

FIG. 15 shows another variation of crimping device (1500) comprising holding structure (1502) having protrusion (1504) and passage units (1506). Protrusion (1504) may serve to provide a space between holding structure (1502) and a self-expanding device (not shown). This space may allow a storage member, applicator, or other device to surround a crimped self-expanding device without pushing downward on the self-expanding device. Alternatively, such a space may be provided by an indentation or gap in a wall of the holding structure.

Figure 16:
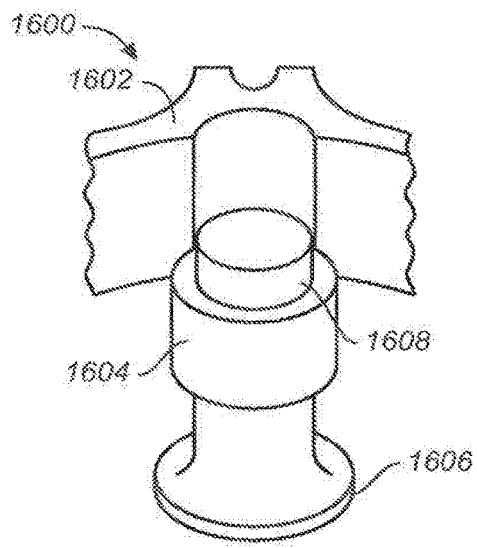

FIG. 16 shows yet another variation of crimping device (1600) comprising holding structure (1602) having an ejector (1604). Ejector (1604) may be used to push a crimped self-expanding device out of crimping device (1600). In some variations, the ejector (1604) may push a crimped self-expanding device from crimping device (1600) into a storage member, an applicator, or other device (not shown). Ejector (1604) may be of any suitable shape, size, or configuration. In some variations, such as shown in FIG. 16, ejector (1604) may operate via pressure placed on a baseplate (1606) of pusher (1608). In other variations, the ejector may be spring-loaded or may be trigger-activated.

Figure 17:
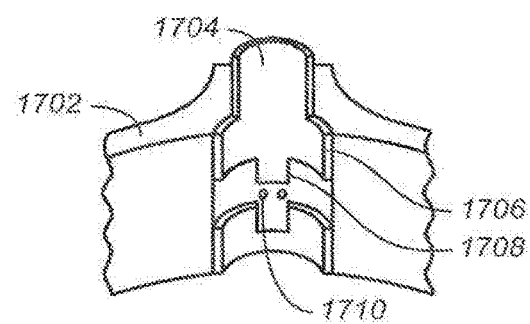

FIG. 17 shows still another variation of crimping device (1700) comprising holding structure (1702) having applicator guide (1704), movable portion (1706), cutting device (1708) and passage units (1710). Cutting device (1708) may be any suitable cutting structure and may be used to sever crimping members (not shown), thereby freeing a self-expanding device (not shown) from holding structure (1702). While shown in FIG. 17 as having one cutting device (1708), crimping device (1700) may have any number of cutting devices (1708). Indeed, crimping device (1700) may have two or more cutting devices (1708) or no cutting device (1708) at all. Additionally, while shown in FIG. 17 as having a movable portion (1706), crimping device (1700) need not. In variations that do include a movable portion (1706), the movable portion may move cutting portion (1708) to sever one or more crimping members. In some variations, movable portion (1706) may move in response to pressure applied by a storage member, applicator, or other device. The downward movement of movable portion (1706) in response to pressure by an applicator may also serve to further guide the applicator around a crimped self-expanding device. In some variations, the movable portion (1706) may be configured to return to its original position when pressure is no longer being applied by an applicator. It should also be appreciated that the crimping devices described here may have any suitable combination of crimping members, holding structures, applicator guides, passage units, shaping portions, cutting devices, movable portions, protrusions and ejectors.

To crimp a self-expanding device using a crimping device comprising one or more crimping members and a holding structure, a self-expanding device is generally placed within the holding structure and one or more of the crimping members engage the self-expanding device. The one or more crimping members may engage self-expanding device in any suitable manner as described above. In methods where the crimping device includes one or more pushers, one or more of the pushers may be pushed through the holding structure to crimp the self-expanding device. In methods in which the crimping device includes one or more crimping members in the form of sutures, wires, guiding hoops, or ribbons, one or more ends of ends of the one or crimping members may be pulled through the holding structure via a passage unit to crimp a self-expanding device. In methods in which the crimping device includes one or more balloons, one or more of the one or more balloons may be inflated to compress the self-expanding device.

Once the self-expanding device has been crimped to an unexpanded configuration, the self-expanding device may be transferred to a storage device, an applicator, or other device. In some methods, an ejector is used to push the self-expanding device into an applicator. In other methods, the applicator removes the self-expanding device from the crimping device. In some methods, the self-expanding device is pushed or pulled through the crimping members. In other methods, the crimping members are severed by a blade. In still other methods, the crimping members may be disengaged from either the self-expanding device or the crimping device as the self-expanding device is placed within an applicator.

In some variations of crimping devices described here, the crimping devices include some combination of crimping portions, storage zones, and applicator engagement portions. FIGS. 18A & 18B show one variation of crimping device (1800) comprising crimping portion (1802), storage zone (1804), and applicator engagement portion (1806). FIG. 18A shows a perspective view of crimping device (1800), while FIG. 18B shows a cutaway view of crimping device (1800).

Generally, crimping portion serves to reduce an expandable member from an expanded configuration to an unexpanded configuration. While shown in FIGS. 18A and 18B as being a funnel with a frustoconical shape, crimping portion (1802) may have any suitable shape or configuration. In some variations, the crimping portion (1802) may have a shape that has irregular geometry or that approximates an oval, triangle, rectangle, polygon, or the like. The crimping portion may additionally include a holding portion configured to hold a self-expanding device in an expanded configuration. In some variations, the crimping portion (1802) may include one or more slits. In variations that include slits, these slits may serve to guide portions of a self-expanding device as it is crimped. Additionally, slits may allow for a pronged-pusher to be advanced through crimping portion (1802), as will be described in more detail below.

While shown in FIGS. 18A & 18B as having a storage zone (1804), the crimping device need not. In variations that do include a storage zone, the storage zone may be configured to house a self-expanding device in its unexpanded configuration. Storage zone (1804) may have any suitable shape or configuration. In some variations, such as that shown in FIGS. 18A & 18B, storage zone may be a cylinder. In other variations, storage zone may be a box, cone, pyramid or curved tube. The storage zone may be detachable from the rest of the crimping device, but need not be. In some variations, storage zone may include one or more blades or cutting members. In other variations, storage zone may include a lip that is configured to allow a self-expanding a device to be pushed through a storage zone in one direction, but resists movement by the self-expanding device in the opposite direction.

While shown in FIGS. 18A and 18B as having an applicator engagement portion (1806), the crimping device (1800) need not. In variations that do include an applicator engagement portion (1806), the applicator engagement portion may have any suitable configuration. Generally, applicator engagement portion (1806) is configured to allow crimping device (1800) to temporarily or permanently attach to an applicator, storage member, or other device. In some of these variations, as illustrated in FIGS. 18A and 18B, applicator engagement portion (1806) is an inlet into which an applicator may be placed. In some of these variations, the end of applicator engagement portion (1806) may flare outward. Alternatively, the applicator engagement portion (1806) may be configured to fit within an applicator.

The crimping device (1800) may additionally include one or more pullers, pushers or other structures for moving a self-expanding device through at least a portion of the crimping device. FIGS. 19A and 19B show side views of one variation of crimping device (1900) having holding portion (1902), crimping portion (1904), storage zone (1906) and puller (1908). Also shown there is self-expanding device (1910). Initially, self-expanding device (1910) may be held in holding portion (1902), as shown in FIG. 19A. Puller (1908) may engage self-expanding device (1910) to draw self-expanding device through crimping portion (1904). As self-expanding device (1910) moves through crimping portion (1904), self-expanding device (1910) may be reduced from an expanded configuration to an unexpanded configuration. In variations in which the crimping device (1900) includes a storage zone (1906), puller (1908) may draw self-expanding device (1910) into storage zone, as shown in FIG. 19B. In these variations, the puller (1908) may then be disengaged from self-expanding device (1910), or may be used to draw self-expanding device into a separate storage member, applicator, or other device. In variations in which the crimping device (1900) does not include a storage zone (1906), puller may draw self-expanding device (1910) directly into a storage member, applicator, or other device.

While shown in FIGS. 19A and 19B as having a handle (1912), sutures (1914), and rings (1916), puller (1908) may have any suitable configuration. In some variations, puller (1908) may include more than one handle. In some variations, one or more of the one or more handles are sized to fit through crimping device (1900). Puller (1908) may additionally include one or more sutures, wires, ribbons, or combinations thereof. In some of these variations, the sutures, wires, or ribbons may include one or more hooks or rings configured for attachment to a self-expanding device. Puller (1908) may engage self-expanding device in any suitable manner as described above.

Figure 20A:
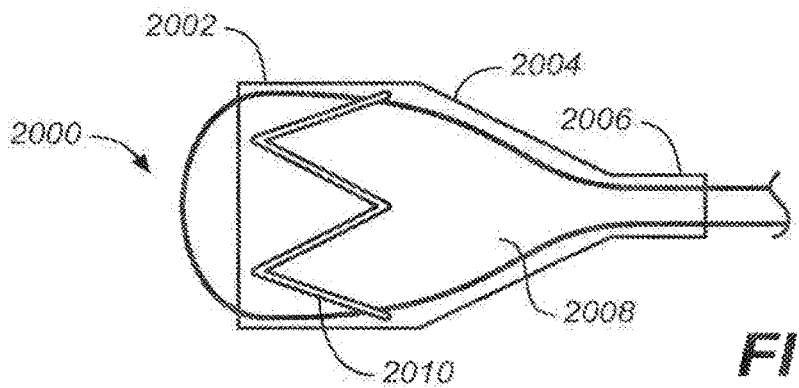
Figure 20B:
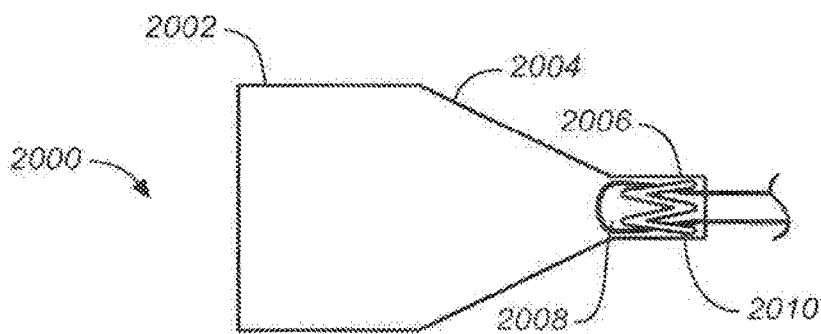

FIGS. 20A and 20B show another variation of crimping device (2000), comprising holding portion (2002), crimping portion (2004), storage zone (2006), and balloon (2008). Also shown there is self-expanding device (2010). As shown in FIG. 20A, balloon (2008) may be inflated inside of crimping device (2000) while self-expanding device (2010) is held within holding portion (2002). Inflation of balloon (2008) may cause balloon (2008) to engage self-expanding device (2010). Balloon (2008) may be withdrawn through crimping device (2000), which in turn may pull self-expanding device (2010) through crimping portion (2004) and into storage zone (2006). Balloon (2008) may be partially deflated as it is withdrawn through crimping device (2000). Balloon (2008) may additionally be used to pull self-expanding device (2010) into a storage member, applicator, or other device. Alternatively, balloon (2008) may be deflated and removed once self-expanding device (2010) has reached storage zone (2006).

Figure 21A:
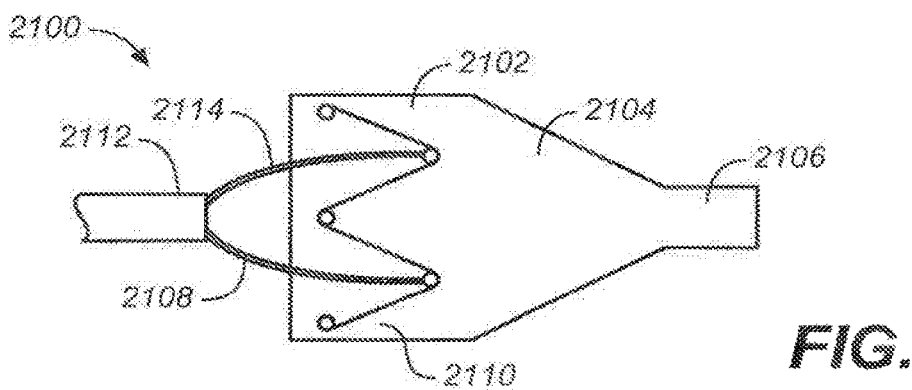
Figure 21B:
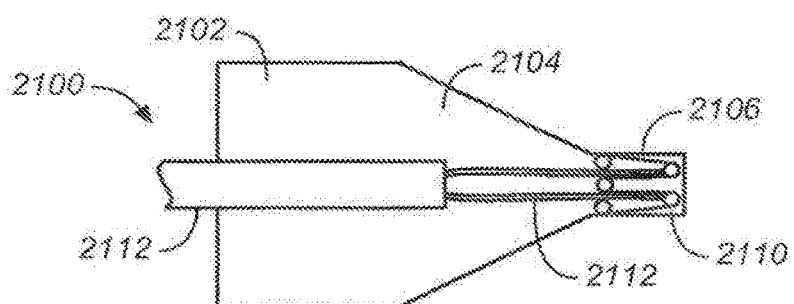

FIGS. 21A and 21B show still another variation of crimping device (2100), comprising holding portion (2102), crimping portion (2104), storage zone (2106) and pusher (2108). Also shown there is self-expanding device (2110). Initially, self-expanding device (2110) may be held in holding portion (2102), as shown in FIG. 21A. Pusher (2108) may engage self-expanding device (2110) to push self-expanding device (2110) through crimping portion (2104). As self-expanding device (2110) moves through crimping portion (2104), self-expanding device (2110) may be reduced from an expanded configuration to an unexpanded configuration. In variations in which the crimping device (2100) includes a storage zone (2106), pusher (2108) may press self-expanding device (2110) into storage zone (2106), as shown in FIG. 21B. In these variations, the pusher (2108) may then be disengaged from self-expanding device (2110), or may alternatively push self-expanding (2110) device into a separate storage member, applicator, or other device. In variations in which the crimping device (2100) does not include a storage zone (2106), pusher (2108) may push self-expanding device (2110) directly into a separate storage member, applicator, or other device.

While shown in FIGS. 21A and 21B as having handle (2112) and semi-rigid wires (2114), pusher (2108) may have any suitable configuration of components. In some variations, pusher (2108) may include more than one handle. Pusher (2108) may additionally include one or more rods, wires, plugs, or combinations thereof. In some of these variations, rods, wires, or plugs may include one or more heads or rings configured for attachment to a self-expanding device. In some variations, pusher (2108) is made of a sponge or similar compressible material that is capable of conforming to the interior of crimping portion (2104). Pusher (2108) may engage self-expanding device in any suitable manner as described above.

Figure 22A:
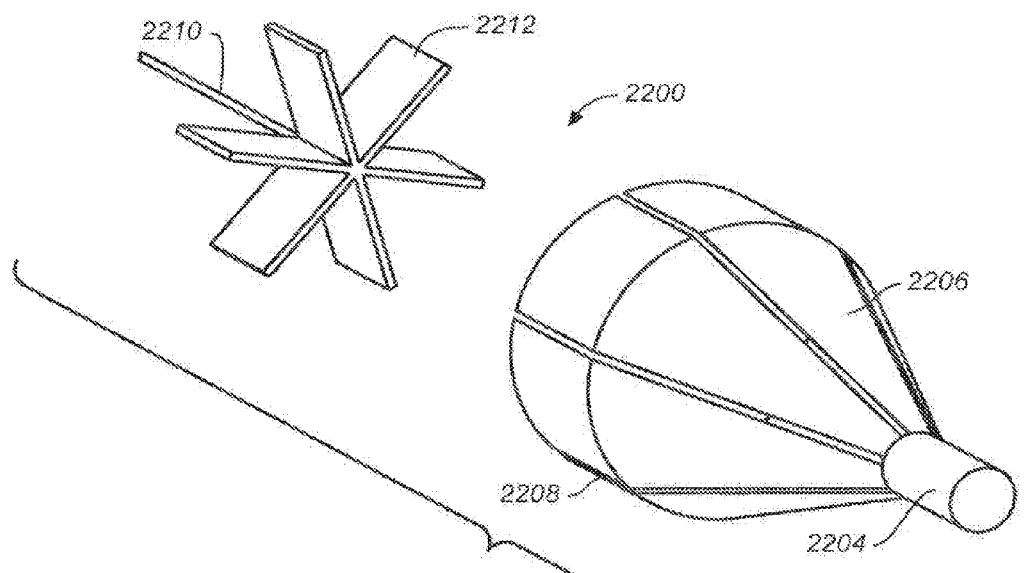
Figure 22B:
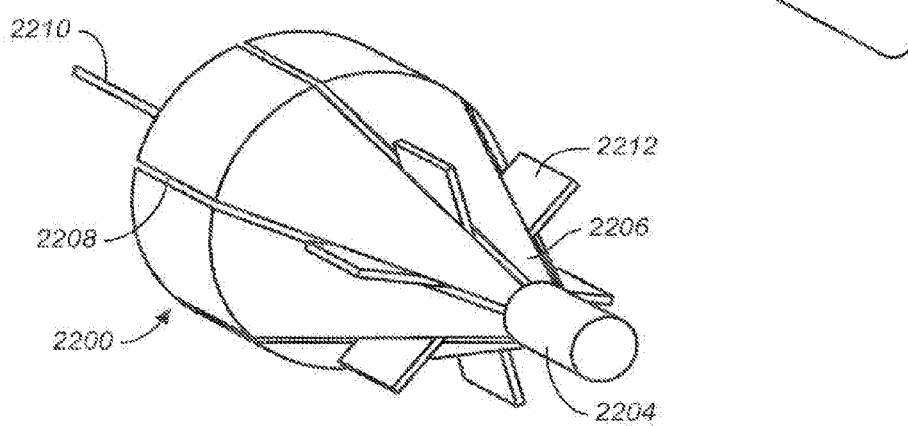
Figure 35A:
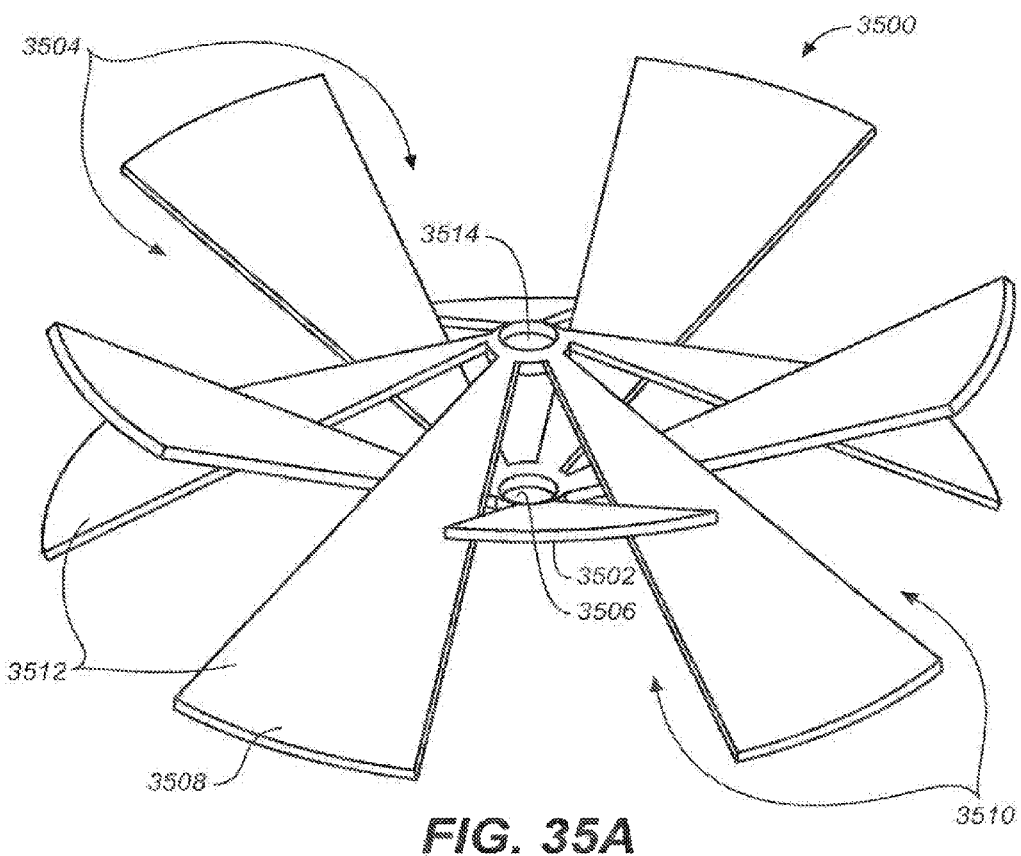
FIGS. 35A and 35B are illustrative depictions of suitable crimping devices having crimping portions.
Figure 35B:
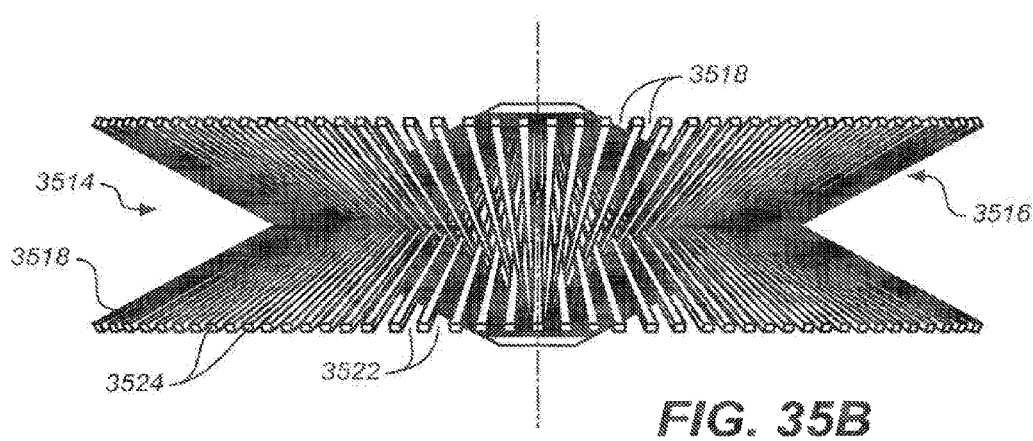

FIGS. 22A and 22B show a variation of crimping device (2200) comprising storage zone (2204), crimping portion (2206) with slits (2208), and pusher (2210) with prongs (2212). Initially, a self-expanding device (not shown) may be placed in crimping device (2200). Pusher (2210) may be moved through crimping portion (2206), and one or more of the prongs (2212) may engage one or more of slits (2208) to guide as shown in FIG. 22B. Pusher (2210) may also engage the self-expanding device. As pusher (2210) is advanced through crimping portion (2206), slits (2208) may guide and control the advancement of pusher (2210). Simultaneously pusher (2210) may also move a self-expanding device through crimping portion (2206), thereby crimping the self-expanding device. Slits (2208) may additionally serve to help guide self-expanding device through crimping portion (2206) as the self-expanding device is crimped. In some variations, the pusher may be a slotted funnel. FIG. 35A shows one such variation of crimping device (3500) comprising crimping portion (3502) with slots (3504) and aperture (3506), and pusher (3508) with slots (3510), prongs (3512), and aperture (3514). The pusher (3508) may engage crimping portion (3502) to crimp a self-expanding device (not shown), as describe above. While shown in FIG. 35A as having five prongs (3512) and five slots (3510), pusher (3508) may have any suitable number of slots (3510) and prongs (3512). For example, FIG. 35B shows a side view of one variation of crimping device (3514) comprising crimping portion (3516) with slots (3518), and pusher (3520) with many slots (3522) and prongs (3524).

Crimping device (2200) may include any number of slits (2208), and slits (2208) may be of any size, shape or configuration. While shown in FIGS. 22A and 22B as extending along the entire length of crimping portion (2206), slits (2208) need not. Indeed, in some variations, slits (2208) may extend only along a portion of crimping portion (2206). In other variations, slits (2208) may extend past crimping portion (2206) and into at least a portion of storage zone (2204).

Any of the features of the crimping devices described here may be automated. For example, in some variations the crimping device comprises a trigger, a button, a combination thereof, or the like. In some of these variations, a trigger or button may be configured to control one or more features a device. For example, activation of a trigger or button may cause a pusher to push a self-expanding member through a crimping portion, or may cause a crimping member to pass through a passage unit. Indeed, triggers or buttons may be used to automate any feature or combination of features described here.

Some variations of the crimping devices described here comprise one or more plates that are engagable to define an aperture. FIGS. 23A and 23B illustrate one variation of crimping device (2300) comprising first (2302) and second (2304) plates that are engaged to define aperture (2306). In some variations, first (2302) and second (2304) plates may be slidably engagable.

Aperture (2306) may define a cross-sectional opening of any size or shape. Indeed, aperture (2306) may be a shape that has irregular geometry or that approximates a diamond, oval, circle, triangle, rectangle, polygon, or the like. Furthermore, aperture (2306) may be symmetrical, but need not be. In variations in which aperture (2306) is symmetrical, it may be symmetrical along any number of axes. Indeed, aperture (2306) may be symmetrical along zero, one, or two axes. In variations where the first (2302) and second (2304) plates are slidably engaged, aperture (2306) may change in size or shape as first (2302) and second (2304) plates are slid relative to each other. For example, as shown in FIG. 23A, aperture (2306) has a shape that approximates a rounded diamond. As first (2302) and second (2304) plates are slid relative to each other, as shown in FIG. 23B, aperture (2306) approximates a circular shape.

While shown in FIGS. 23A and 23B as having two plates, crimping device (2300) may have any number of plates. Indeed, in some variations, the crimping device may have three or more plates. FIGS. 24A and 24B show one such variation of crimping device (2400) having first (2402), second (2404), and third plates (2406). Also shown there are holding portions (2408). In variations where crimping device (2400) includes three or more plates, each plate may be slidably engagable with all, some, or none of the remaining plates. Furthermore, each plate may be fixedly attached to all, some, or none of the remaining plates.

In variations of crimping device (2400) that include three or more plates, each plate may define an aperture with any other plate. Thus, crimping member (2400) may define two or more apertures. Each of these apertures may have the same size and shape, but they need not. Indeed, in some variations different apertures may have different sizes or different shapes. As such, variations of crimping device (2400) that include three or more plates may find particular utility in situations in which non-uniform crimping of a self-expanding device is desirable.

Additionally, crimping device (2400) may include one or more features that may aid in the crimping of a self-expanding device. In some variations, crimping device (2400) may include spacers located between all, some, or none of the plates. In other variations, crimping device (2400) may include one or more handles that may aid in handling or operating crimping device (2400). In still other variations, such as the variations shown in FIGS. 24A and 24B, crimping device (2400) may include one or more extenders (2408). Generally, extenders (2408) may help to hold portions of a self-expanding device (not shown) that is not engaged by the plates. In some variations, multiple extenders (2408) may interact to completely enclose a self-expanding device as the aperture or apertures defined by the plates is reduced, as shown in FIG. 24B. Additionally, extenders (2408) may engage a storage member, applicator, or other device to facilitate retrieval of the self-expanding device. Extenders may also act to hold a crimped self-expanding device in a certain shape.

While shown in FIGS. 24A and 24B as being located on first (2402), second (2404), and third (2406) plates, extenders may be affixed to or formed on any number of plates. Indeed, extenders may be placed on all, some, or none of the plates. Similarly, each plate may include any number of extenders. For example, in the variation shown in FIG. 24A, first (2402) and third plates (2406) each have one extender (2408), while second plate (2404) has two extenders (2408).

Generally, the crimping devices described above may be used to crimp a self-expanding device to a reduced configuration. In these methods, the self-expanding may be placed in one or more apertures defined by the crimping device. As some or all of the plates are moved, one or more of the one or more apertures may change shape and/or size. As the size of the aperture is decreased the self-expanding device becomes crimped. The crimped self-expanding device may then be placed in a storage member, applicator, or other device.

Figure 36A:
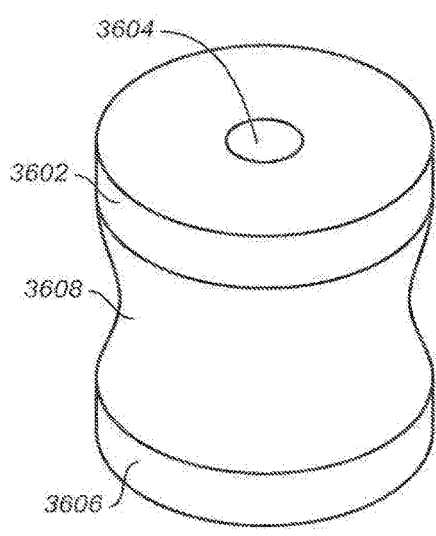
Figure 36B:
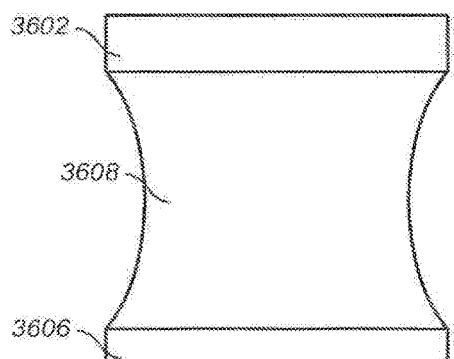
Figure 36C:
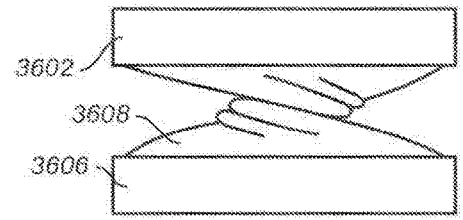

Some variations of the crimping devices described here include one or more crimping tubes. FIGS. 36A-36F show one variation of crimping device (3600) comprising top plate (3602) having funnel (3604), bottom plate (3606), and crimping tube (3608). Generally, crimping tube (3608) may be attached between top (3602) and bottom (3606) plates, as shown in a perspective view in FIG. 36A and in a cutaway view in FIG. 36B. Crimping tube (3608) may be made from or comprise any suitable flexible material, such as, for example, latex. When top plate (3602) is rotated relative to bottom plate (3606), crimping tube (3608) may wrap around itself, reducing the diameter of crimping tube (3608) and bringing top (3602) and bottom (3606) plates closer together, as seen in FIG. 36C.

Figure 36D:
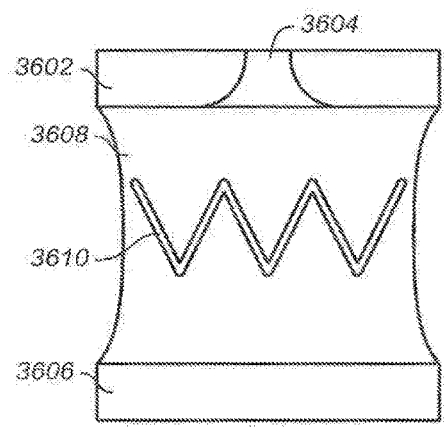
Figure 36E:
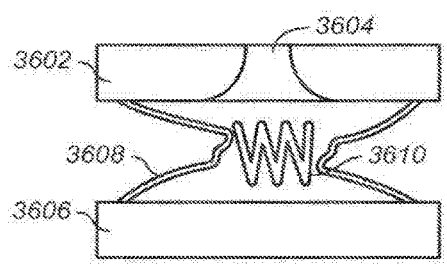
Figure 36F:
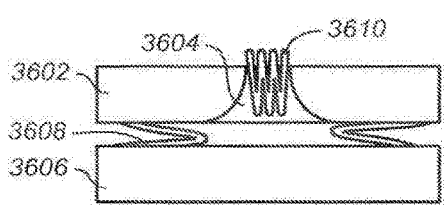

Crimping device (3600) may be used to crimp a self-expanding device (3610). Generally, self-expanding device (3610) may be placed within crimping tube (3608), as shown in FIG. 36D. When top plate (3602) and bottom plate (3606) are rotated relative to each other, crimping tube (3608) may reduce in diameter to engage and crimp self-expanding device (3610), as shown in FIG. 36E. Once the self-expanding device (3610) is crimped, the self-expanding device (3610) may be ejected from crimping device (3600) through funnel (3604) by pushing top (3602) and bottom (3606) plates together.

Figure 37A:
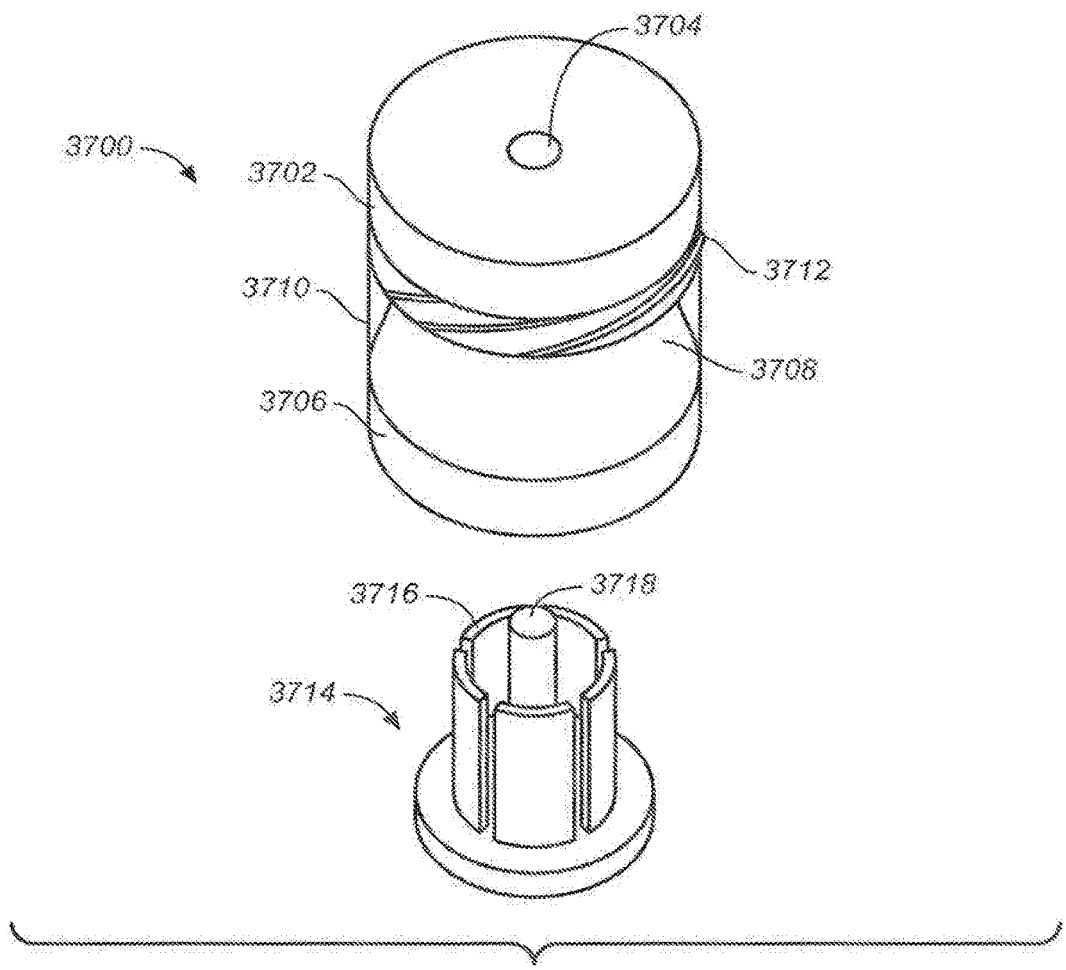

In some variations, a crimping device comprising a crimping tube may additionally comprise a holding structure. FIGS. 37A-37E show one variation of crimping device (3700) comprising top plate (3702) including funnel (3704), bottom plate (3706), crimping tube (3708), cylinder (3710) having threading (3712), and holding structure (3714) having prongs (3716) and pusher (3718). Also shown there is self-expanding device (3720). Generally, crimping tube (3708) may be attached between top (3702) and bottom (3704) plates, as shown in FIG. 37A. Additionally, prongs (3716) and pusher (3718) may be able to pass through corresponding slots (not shown) in bottom plate (3706).

Figure 37B:
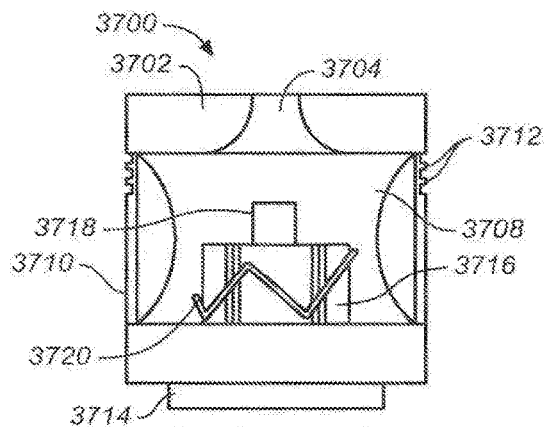
Figure 37D:
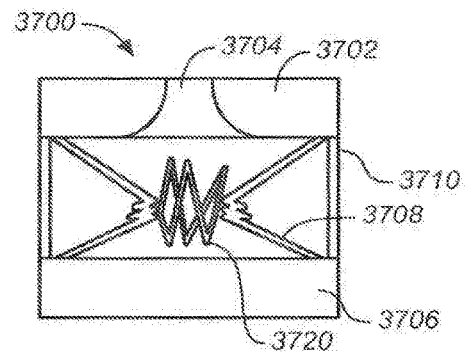
Figure 37C:
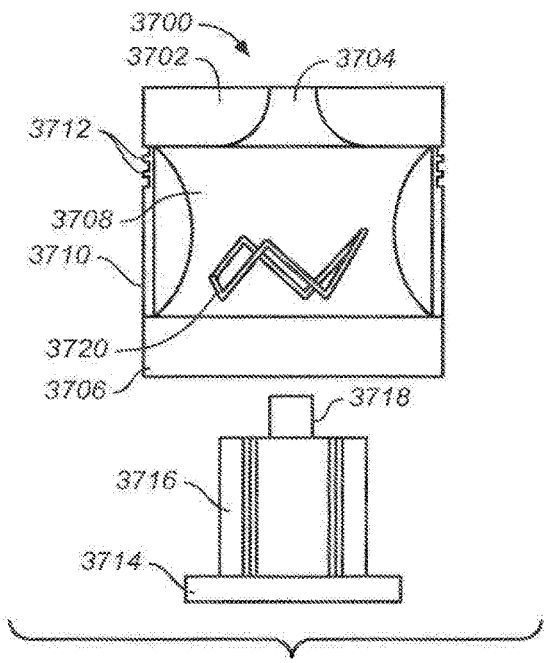
Figure 37E:
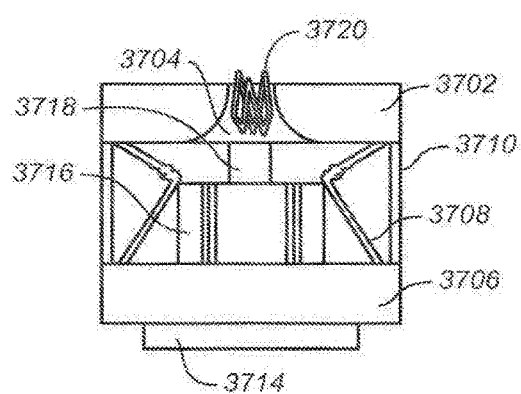

To crimp a self-expanding device (3720) using crimping device (3700), holding structure (3714) may be inserted into bottom plate (3706) such that prongs (3716) and pusher (3718) extend through the corresponding slots in bottom plate (3706). A self-expanding device (3720) may then be placed around prongs (3716), and stored in an expanded configuration inside of crimping tube (3708), as shown in FIG. 37B. When the self-expanding device (3720) is ready to be crimped, holding structure (3714) may be withdrawn from bottom plate (3706), which may in turn leave self-expanding device within crimping tube (3708), as shown in FIG. 37C. Top plate (3702) may be rotated relative to bottom plate (3706), thereby reducing the diameter of crimping tube (3708) and crimping self-expanding device (3720), as shown in FIG. 37D. This rotation may be guided by grooves (not shown) in top plate (3702) that engage threading (3712) of cylinder (3710). Once the self-expanding device (3720) has been crimped, it may be ejected or removed from crimping device (3700). In some variations, the self-expanding device (3720) is ejected from crimping device (3700) by reinserting holding structure (3714) into bottom plate (3706) such that pusher (3718) engages self-expanding device (3720) to push it through funnel (3704) of top plate (3702).

While shown in FIGS. 37A-37E as having prongs (3716) and pusher (3718), holding structure (3714) may have any configuration. In some variations, holding structure (3714) may have prongs (3716) but no pusher (3718). In some variations, crimping device (3700) has a pusher (3718) that is separate from holding structure (3714). In variations that include prongs (3716), holding structure (3714) may comprise any number of prongs (3716). Indeed, holding structure may have zero, one, or two or more prongs (3716). Furthermore, these prongs may be sized and shaped to hold a self-expanding device (3720) in an expanded configuration. In some variations, the configuration of prongs (3716) may be determined by or based upon the size and shape of the self-expanding device (3720) in an expanded configuration. In other variations, the prongs (3716) may be configured to hold a self-expanding device (3720) in a certain shape.

Additionally, while shown in FIGS. 37A-37E as having a cylinder (3710) with threading (3712), crimping device (3700) need not. In variations that do include a cylinder (3710), cylinder (3710) may help to keep bottom plate (3706) positioned relative to top plate (3702). Additionally, threading (3712) may limit the amount of rotation that occurs between top plate (3702) and bottom plate (3706).

In some variations, a crimping device comprising a crimping tube may additionally comprise guide cylinders. FIGS. 38A-38F show one variation of crimping device (3800) comprising top plate (3802) having slots (3804), funnel (3806) and top guide cylinder (3808) with protrusions (3810), crimping tube (3812), and bottom plate (3814) having slots (3804), funnel (3806), and bottom guide cylinder (3816) with indentations (3818). Also shown there is holding structure (3820) with prongs (3822). FIG. 38B shows a perspective view of crimping device (3800), while FIG. 38A shows a perspective view of crimping device (3800) without crimping tube (3812). In some variations, crimping tube may be attached between top plate (3802) and bottom plate (3814). Furthermore, protrusions (3810) of top guide cylinder (3808) are configured to engage indentations (3818) of bottom guide cylinder (3816) to allow top guide cylinder (3808) to slide within bottom guide cylinder (3816). Additionally, prongs (3822) of holding structure (3820) may be able to pass through corresponding slots (3804) on either top (3802) or bottom (3814) plates.

To crimp a self-expanding device (not shown) using crimping device (3800), holding structure (3820) may be inserted into bottom plate (3814) such that prongs (3822) extend through the corresponding slots (3804) in bottom plate (3814), as shown in FIG. 38C. In some variations, holding structure (3820) may be instead be inserted into top plate (3802). A self-expanding device may then be placed around prongs (3822) and stored in an expanded configuration inside of crimping tube (3812). When the self-expanding device is ready to be crimped, holding structure (3820) may be withdrawn from bottom plate (3816), as shown in FIG. 38D. This may in turn leave self-expanding device within crimping tube (3812). Top plate (3802) may be rotated relative to bottom plate (3814), as shown in FIG. 38E. This may reduce the diameter of crimping tube (3812), crimp the self-expanding device, and align protrusions (3810) and indentations (3818). Once protrusions (3810) and indentations (3818) are aligned, top (3802) and bottom (3814) plates may be pushed together, causing top guide cylinder (3808) to slide within bottom guide cylinder (3816), as shown in FIG. 38F. In some variations, the self-expanding device may then be ejected from crimping device (3800) through funnel (3804) of either top (3802) or bottom (3814) plates using a pusher or other ejector.

Top (3808) and bottom (3816) guide cylinders may have any suitable number of indentations (3818) and protrusions (3810). Furthermore, these indentations (3818) and protrusions (3810) may have any suitable shape and size. Different protrusions (3810) may have the same size and shape, or may have different sizes or shapes. Similarly, different indentations (3818) may have the same size and shape, or may have different sizes or shape. In some variations, each protrusion (3810) may be configured to be able to engage only one indentation (3818). In other variations, each protrusion (3810) may be configured to be able to engage two or more indentations (3818).

While the crimping devices described above have generally been configured to crimp one self-expanding device, any of the crimping devices described above may also be configured to crimp any number of self-expanding devices. In some variations, two or more self-expanding devices may be crimped sequentially. In some of these variations, the same crimping device is reusable to crimp any number of self-expanding devices. In other variations, two or more self-expanding device may be crimped simultaneously. Additionally, the two or more crimped self-expanding devices may be transferred into the same storage member, applicator or other device, or may be transferred into two or more storage members, applicators, or other devices. In some variations, the crimping devices may have one crimping member that engages multiple self-expanding devices to crimp the self-expanding devices. In other variations, the crimping devices may have a plurality of crimping members, where each crimping member engages one or more self-expanding devices to crimp the one or more self-expanding devices.

Figure 39:
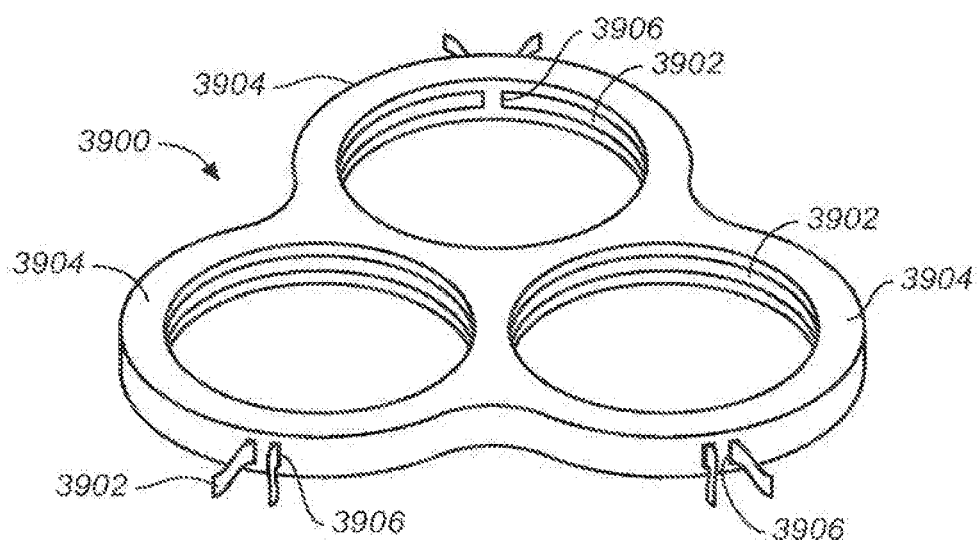
FIGS. 39 and 40 depict illustrative variations of crimping devices that may crimp multiple self-expanding devices.

FIG. 39 illustrates one variation of crimping device (3900) that may be capable of crimping multiple self expanding devices (not shown). Shown there are crimping members (3902) and holding structures (3904) having passage units (3906). In some variations, each holding structure (3904) may be configured to crimp one or more self-expanding device. While shown in FIG. 39 as having three holding structures (3904), crimping device (3900) may have any suitable number of holding structures (3904). Additionally, each holding structure (3904), passage unit (3906), and crimping member (3902) may have any suitable configuration or combination of features as described above.

Figure 40:
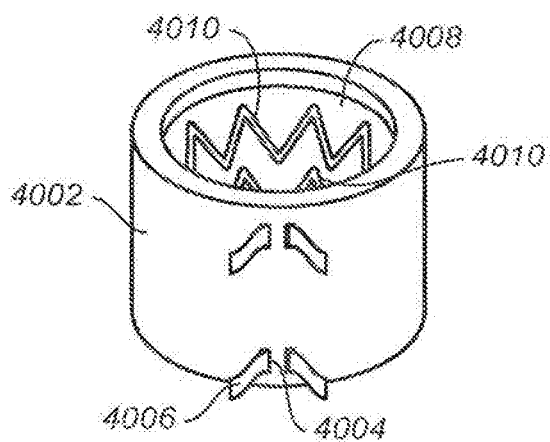

FIG. 40 shows another variation of crimping device (4000) that may be capable of crimping multiple self-expanding devices (not shown). Shown there is holding structure (4002) with passage units (4004) and crimping members (4006) having sheath (4008) and handle (4010). In these variations, sheath (4008) may be sized to hold two or more self-expanding devices. When the crimping members (4006) are pulled through passage units (4004), the sheath (4008) may engage the two or more self-expanding devices. This engagement may crimp the two or more self-expanding devices simultaneously.

Also described here are kits. These kits may comprise any suitable components. For example, the kits may comprise one or more self-expanding device, and one or more of the crimping devices described above. The kits may also comprise instructions for using any of the kit components, or assembling any of the kit components. In some variations, the kits include separate, unassembled components of the crimping device. In some of these variations, the kit may also include one or more tools to help with assembly of the crimping device. In some variations, the kits may include one or more storage members, applicators, or other devices. In other variations, the kits may include one or more storage structures for storing one or more self-expanding device in an expanded configuration.

What we claim is:

1. A crimping device for crimping a self-expanding device having an unexpanded configuration and an expanded configuration, the crimping device comprising:
   a holding structure, the holding structure comprising a hoop configured to hold therein the self-expanding device in its expanded configuration, the hoop comprising at least one passage unit; and
   a crimping member positioned in the holding structure, wherein a first end portion of the crimping member extends through the at least one passage unit, wherein movement of the first end portion of the crimping member through the at least one passage unit reduces the amount of crimping member in the holding structure and causes the crimping device to reduce the self-expanding device to its unexpanded configuration.

2. The crimping device of claim 1, wherein the self-expanding device is biodegradable.

3. The crimping device of claim 1, wherein the crimping member comprises a ribbon.

4. The crimping device of claim 1, wherein the passage unit comprises a slot.

5. The crimping device of claim 1, wherein a second end portion of the crimping member remains in the interior of the holding structure during movement of the first end portion through the at least one passage unit.

6. The crimping device of claim 1, wherein the crimping member is configured to wrap around the self-expanding device and sit between the self-expanding device and the holding structure.

7. The crimping device of claim 1, wherein the holding structure comprises at least two separate components that together form the holding structure.

8. The crimping device of claim 1, wherein the holding structure defines an aperture through which the self-expanding device may be retrieved when the self-expanding device is in its unexpanded configuration.

* * * * *